United States Patent
Cai et al.

(10) Patent No.: US 10,919,899 B2
(45) Date of Patent: Feb. 16, 2021

(54) IMIDAZOPYRAZINE COMPOUNDS, PREPARATION METHODS AND USES THEREOF

(71) Applicant: DONGGUAN ZHENXING-BEITE MEDICINE TECHNOLOGY CO., LTD., Dongguan (CN)

(72) Inventors: Xiong Cai, Dongguan (CN); Xianbin Zhong, Dongguan (CN); Chunqiang Ye, Dongguan (CN); Qijie He, Dongguan (CN); Shifeng Qin, Dongguan (CN); Changgeng Qian, Dongguan (CN)

(73) Assignee: DONGGUAN ZHENXING-BEITE MEDICINE TECHNOLOGY CO., LTD., Dongguan (CN)

( * ) Notice: Subject to any disclaimer, the term of this patent is extended or adjusted under 35 U.S.C. 154(b) by 0 days.

(21) Appl. No.: 16/478,042

(22) PCT Filed: Jan. 15, 2018

(86) PCT No.: PCT/CN2018/072581
§ 371 (c)(1),
(2) Date: Jul. 15, 2019

(87) PCT Pub. No.: WO2018/130213
PCT Pub. Date: Jul. 19, 2018

(65) Prior Publication Data
US 2019/0367524 A1    Dec. 5, 2019

(30) Foreign Application Priority Data
Jan. 16, 2017   (CN) .......................... 2017 1 0028449

(51) Int. Cl.
*C07D 487/04* (2006.01)
*A61K 31/4985* (2006.01)

(52) U.S. Cl.
CPC ........ *C07D 487/04* (2013.01); *A61K 31/4985* (2013.01)

(58) Field of Classification Search
CPC .......................... C07D 487/04; A61K 31/4985
See application file for complete search history.

(56) References Cited

U.S. PATENT DOCUMENTS

| 9,290,504 | B2 | 3/2016 | Barf et al. |
| 9,718,828 | B2 | 8/2017 | De Man et al. |

FOREIGN PATENT DOCUMENTS

| CN | 101674834 A | 3/2010 |
| CN | 103889987 A | 6/2014 |
| CN | 103917545 A | 7/2014 |
| CN | 105753863 A | 7/2016 |
| CN | 106588937 A | 4/2017 |
| EP | 2139487 B1 | 11/2015 |
| JP | 2010526768 A | 8/2010 |
| JP | 2014520866 A | 8/2014 |
| JP | 2014520870 A | 8/2014 |
| JP | 2015537033 A | 12/2015 |
| JP | 2015509927 A | 3/2016 |
| JP | 2016540053 A | 12/2016 |
| WO | 2010065898 A3 | 6/2010 |

(Continued)

OTHER PUBLICATIONS

P. Wu et al., 36 Trends in Pharmacological Sciences, 422-439 (2015) (Year: 2015).*
Z. Wang et al., 19 Drug Discovery Today, 145-150 (2014) (Year: 2014).*
U.K. Marelli et al., 3 Frontiers in Oncology, 1-12 (2013) (Year: 2013).*
A. Kooistra et al., Kinase-Centric Computational Drug Development, In 50 Annual Reports in Medicinal Chemistry, 197-236 (2017) (Year: 2017).*
P. Chène, 13 Drug Discovery Today, (2008) (Year: 2008).*
K-H Kim et al., 21 Bioorganic & Medicinal Chemistry Letters, 6258-6263 (2011) (Year: 2011).*

(Continued)

*Primary Examiner* — Deepak R Rao
(74) *Attorney, Agent, or Firm* — Kagan Binder, PLLC

(57) ABSTRACT

Disclosed are an imidazopyrazine compound, a preparation method therefor and use thereof. Specifically, disclosed are a compound having a structure as represented by formula (I), a pharmaceutically acceptable salt, a stereoisomer or a prodrug thereof, and use of the compound, the pharmaceutically acceptable salt, the stereoisomer or the prodrug thereof in the preparation of a medicament. The medicament is used for preventing and/or treating diseases and/or conditions related to Bruton's tyrosine kinase overactivity in a subject. Further disclosed is use of the compound, the pharmaceutically acceptable salt, the stereoisomer or the prodrug thereof in the preparation of a formulation. The formulation is used for reducing or inhibiting the activity of the Bruton's tyrosine kinase in cells.

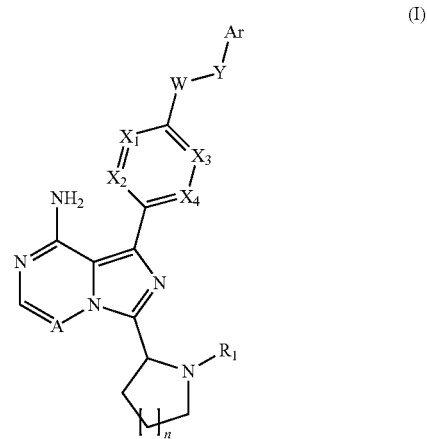

19 Claims, 2 Drawing Sheets

(56) References Cited

FOREIGN PATENT DOCUMENTS

| WO | 2011152351 | A1 | 12/2011 | |
|---|---|---|---|---|
| WO | 2013116382 | A1 | 8/2013 | |
| WO | 2014078578 | A1 | 5/2014 | |
| WO | 2015057992 | A1 | 4/2015 | |
| WO | 2015083008 | A1 | 6/2015 | |
| WO | 2015132799 | A3 | 9/2015 | |
| WO | 2016087994 | A1 | 6/2016 | |
| WO | 2016105582 | A1 | 6/2016 | |
| WO | 2016106623 | A1 | 7/2016 | |
| WO | 2016106624 | A1 | 7/2016 | |
| WO | 2016128912 | A1 | 8/2016 | |
| WO | 2016192074 | A1 | 12/2016 | |
| WO | 2017041536 | A1 | 3/2017 | |
| WO | WO-2018001331 | A1 * | 1/2018 | ............. A61P 19/04 |

OTHER PUBLICATIONS

Z. Pan et al., 2 ChemMedChem, 58-61 (2007) (Year: 2007).*
A. Flemming et al., 9 Nature Reviews | Drug Discovery (2010) (Year: 2010).*
L.R. Whyburn et al., 171 Journal of Immunology, 1850-1858 (2003) (Year: 2003).*
A.O. Vassilev et al., 10 Current Pharmaceutical Design, 1757-1766 (2004) (Year: 2004).*
Faith Uckun et al., 136 British Journal of Haematology, 574-589 (2007) (Year: 2007).*
R.W. Hendriks et al., 18 Seminars in Immunology, 67-76 (2006) (Year: 2006).*
Faith Uckun et al., 20 Expert Opinion on Therapeutic Patents, 1457-1470 (2010) (Year: 2010).*
J. Rautio et al., 17 Nature Reviews Drug Discovery (2018) (Year: 2018).*
Pearce et al., Failure modes in anticancer drug discovery and development, Cancer Drug Design and Discovery Edited by Stephen Neidle, Chapter 18, pp. 424-435 (2008).*
Simone, Oncology: Introduction, Cecil Textbook of Medicine, 20th Edition, vol. 1, pp. 1004-101 O, 1995.*
Johnson et al., Relationships between drug activity in NCI preclinical in vitro and in vivo models and early clinical trials, British Journal of Cancer, 84(10):1424-1431, 2001.*
Gura et al., Systems for identifying new drugs are often faulty, Science, 278:1041-1042, 1997.*
ten Hacken et al., Microenvironment dependency in Chronic Lymphocytic Leukemia: The basis for new targeted therapies, 11 pages, Pharmacology & Therapeutics 144, (2014) pp. 338-348.*
Acute Leukemia, Merck Manual (Online Edition) 6 pages, pp. 1-6 (2013).*
English Translation of International Search Report for International Application No. PCT/CN2018/072581, dated Mar. 9, 2018 (6 pages).
First Search Report for Chinese Application No. 201710028449.2 (1 page).
First Office Action, and English Translation thereof, for Chinese Application No. 201710028449.2, dated Jan. 2, 2018 (18 pages).
Second Office Action, and English Translation thereof, for Chinese Application No. 201710028449.2, dated May 9, 2018 (17 pages).
Supplementary Search Report for Chinese Application No. 201710028449.2 (1 page).
Extended European Search Report for European Application No. 18738713.9, dated Jul. 8, 2020, (7 pages).
First Search Report for Japanese, and English Translation thereof, for Japanese Application No. 2019-559150, dated Aug. 4, 2020, (6 pages).
Byrd et al., "Acalabrutinib (ACP-196) in Relapsed Chronic Lymphocytic Leukemia", The new England journal of medicine, vol. 374, No. 4, pp. 323-332, 2016, (10 pages).

* cited by examiner

IMIDAZOPYRAZINE COMPOUNDS, PREPARATION METHODS AND USES THEREOF

TECHNICAL FIELD

The present disclosure belongs to the technical field of medicines and relates to an imidazopyrazine compound, a method of preparing the compound, and a use of the compound in the preparation of a drug. The drug is used for preventing and/or treating a disease and/or a condition of a subject associated with overactivity of Bruton's tyrosine kinase.

BACKGROUND

Bruton's tyrosine kinase (BTK) is a key signaling molecule in a B-cell receptor signaling complex and is a key protein kinase for survival and proliferation of a lymphocyte. BTK plays an important role in survival and spreading of a malignant B-cell.

A BTK inhibitor has an anticancer effect by inhibiting a tumor cell BTK. The first BTK inhibitor Ibrutinib is a 4'-aminopyrazolo[3,4-d]pyrimidine compound (Honigberg, L. A., et al. Proc Natl Acad Sci USA, 107: 13075, 2010), which inhibits BTK irreversibly by selectively and covalently binding with an active site cysteine remainder (Cys-481) of a target protein BTK so as to effectively prevent a migration of a tumor from a B-cell to a lymphoid tissue which adapts to a tumor growth environment. Since 2013, Ibrutinib was approved by the American FDA for the treatments of refractory mantle cell lymphoma (MCL), refractory chronic lymphocytic leukemia (CLL), mutant CCL with 17p deletion (del 17p), and primary macroglobulinemia.

Except for Ibrutinib, BTK inhibitors AVL-292 (CC292), ONO-4059 BGB-3111, and Acalabrutinib (ACP-196) are also in the clinical development stage for treatments of B-cell non4iodgkinlymphoma, chronic lymphocytic leukemia, multiple myeloma, hairy cell leukemia, adult acute lymphoblastic leukemia, and the like. A combination therapy of Ibrutinib with a chemotherapy drug or other targeted anticancer drug can improve curative effect on the tumor. In clinical test, a drug which can be used in combination with the BTK inhibitor includes rituximab, lenalidomide, fludarabine, cyclophosphamide, adriamycin, vincristine, and prednisone.

BIK: activity in primitive cells of about 80% of acute myelogenous leukemia (AML) patients is increased as compared to that in the normal hematopoietic cells, which causes the cells to be sensitive to oral BTK inhibitor .Ibrutinib in vitro (Marcel Spaargaren M. Lancet Heamat. 2: e180, 2015). A clinical research of treatment of acute myelogenous leukemia by administrating Ibrutinib only or in combination with cytosine arabinoside has entered phase II clinical stage.

In recent years, it has found that BTK is expressed in a cell and a tissue of a solid tumor, such as prostate cancer, and the expression level is in connection with the cancer grading (Guo W. et al. Cell Death Dis. 5: e1409, 2014). BTK inhibits B-cell and macrophage BTK and recovers the T-cell dependent antitumor immune response (Gunderson A. J. et al, Cancer Discov. 6: 270, 2016). A phase II clinical trial of using Ibrutinib and Acalabrutinib to treat various solid tumors, such as NSCLC, breast cancer, prostate cancer, stomach cancer, colon cancer, and the like, is in development (Clinical Trials. gov)

The effect of BTK in a B-cell receptor (BCR) messenger system is very important in the process of development and activation of a normal B-cell. The BCR signal abnormality is associated with an autoimmune disease, such as rheumatoid arthritis (RA). Besides, BTK is also expressed in a myeloid cell including a monocyte, a macrophage, a neutrophil, and a mast cell. These cells infiltrate the synovial membrane cavity and generate inflammatory cytokines thereby aggravating a condition of arthritis. The BTK inhibitor can block dependent cell proliferation of a B-cell receptor and reduce generation of inflammatory cytokines (Whang J. A., Chang B. Y. Drug Discov Today. 19: 1200, 2014). Preclinical studies show that the BTK inhibitor is also effective to a variety of inflammations and autoimmune diseases, such as an animal model of rheumatoid arthritis. Except for rheumatoid arthritis and lupus erythematosus, this kind of drug has possibility to be used for lupus nephritis, multiple sclerosis, Sjogren's syndrome, underlying disease asthma, and so on. A use of the BTK inhibitor, such as CC-292 and 111M71224, for treatment of autoimmune disease, such as rheumatoid arthritis, has entered the clinical trial stage (Clinical Trials, gov ID: NCT01.975610, NCT01765478).

Acalabrutinib (ACP-196) is a second generation BTK inhibitor and has a higher selectivity to BTK than to other kinases. Acalabrutinib does not inhibit EGFR, ITK, and TEC and has no influence on phosphorylation of EGFR at Y1068 locus and Y1173 locus. Acalabrutinib has a higher $IC_{50}$ value than the first generation BTK inhibitor Ibrutinib. Unlike the first generation BTK inhibitor, preclinical and clinical experimental data show that Acalabrutinib can block the BTK pathway selectively without influence on the normal EGFR and will not destroy the key molecule pathway maintaining blood platelets and immunologic function, thereby avoiding or reducing some untoward effects associated with cancer treatment (Byrd J. C. et at N Engl J Med 374: 323, 2016).

The above studies all show that the BTK inhibitor, especially selective BTK inhibitor, as a drug for preventing and treating tumors, a variety of inflammations, and autoimmune diseases, has a great potential value.

SUMMARY

Based upon extensive research, the inventors have found that a compound as represented by formula (I) has a BTK inhibitory activity and thus can function as a BTK inhibitor, for example, the compound can be used for preventing and/or treating a disease associated with the BTK, such as tumor, inflammation and autoimmune disease.

Therefore, one aspect of the present disclosure relates to a compound having a structure as represented by formula (I), a pharmaceutically acceptable salt thereof, a stereoisomer thereof, or a prodrug thereof:

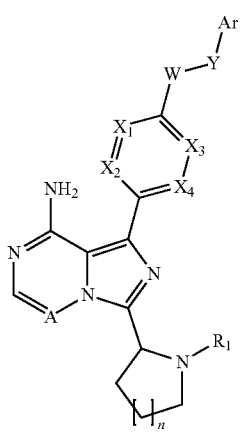

(I)

wherein,
A is selected from CH or N;
n is 0, 1, 2, or 3;
$R_1$ is selected from the following groups:

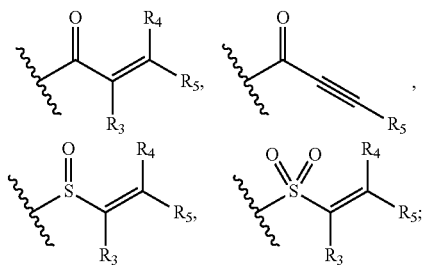

wherein $R_3$ and $R_4$ are each independently selected from H and $C_1$-$C_6$ alkyl;

$R_5$ is selected from H, $C_1$-$C_6$ alkyl, $C_3$-$C_6$ cycloalkyl, $C_1$-$C_4$ alkyl substituted with $C_1$-$C_3$ alkoxy, $C_1$-$C_4$ alkyl substituted with amino, $C_1$-$C_4$ alkyl substituted with $C_1$-$C_3$ alkyl amino, $C_1$-$C_4$ alkyl substituted with di($C_1$-$C_3$ alkyl) amino, and $C_1$-$C_4$ alkyl substituted with a heterocyclic group;

$X_1$, $X_2$, $X_3$, and $X_4$ are each independently selected from $C(R_2)$ and N;

$R_2$ is selected from H, halogen atom, $C_1$-$C_6$ alkyl, $C_1$-$C_6$ alkoxy, and halogenated $C_1$-$C_6$ alkyl;

W and Y are each independently selected from O, $N(R_6)$, S, and $C_1$-$C_6$ alkylene, and at least one of W and Y is selected from $C_1$-$C_6$ alkylene;

$R_6$ is selected from H or $C_3$-$C_6$ alkyl;

Ar is selected from phenyl or 5 to 6 membered heteroaryl (such as 5 to 6 membered nitrogen-containing heteroaryl), optionally, the phenyl or 5 to 6 membered heteroaryl is substituted with a group selected from halogen atom, $C_1$-$C_6$ alkyl, $C_1$-$C_6$ alkoxy, and halogenated $C_1$-$C_6$ alkyl.

In some embodiments, A is CH.

In some embodiments, $X_1$, $X_2$, $X_3$, and $X_4$ are each selected from $C(R_2)$; or one of $X_1$, $X_2$, $X_3$, and $X_1$ is N and the remaining are each selected from $C(R_2)$.

In some embodiments, $X_1$, $X_2$, $X_3$, and $X_4$ are each CH.

In some embodiments, $X_1$ is N and $X_2$, $X_3$, and $X_4$ are each selected from $C(R_2)$, more preferably, $X_2$, $X_3$, and $X_4$ are each CH.

In some embodiments, $X_2$ is N and $X_1$, $X_3$, and $X_4$ are each selected from $C(R_2)$, more preferably, $X_1$, $X_3$, and $X_4$ are each CH.

In some embodiments, $X_3$ is N and $X_1$, $X_2$, and $X_4$ are each selected from $C(R_2)$, more preferably, $X_1$, $X_2$, and $X_4$ are each CH.

In some embodiments, $X_4$ is N and $X_1$, $X_2$, and $X_3$ are each selected from $C(R_2)$, more preferably, $X_1$, $X_2$, and $X_3$ are each CH.

In some embodiments, the compound has a structure as represented by formula (II):

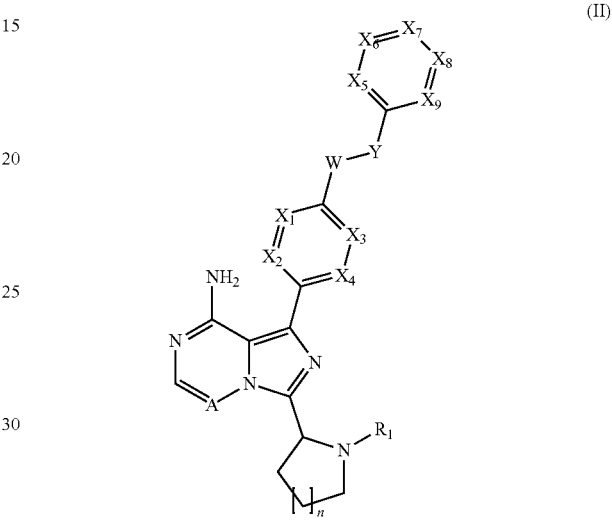

(II)

wherein $X_5$, $X_6$, $X_7$, $X_8$, and $X_9$ are each independently selected from $C(R_7)$ or N;

$R_7$ is selected from H, halogen atom, $C_1$-$C_6$ alkyl, $C_1$-$C_6$ alkoxy, and halogenated $C_1$-$C_6$ alkyl.

In some embodiments, $X_5$, $X_6$, $X_7$, $X_8$, and $X_9$ are each selected from $C(R_7)$; or one of $X_5$, $X_6$, $X_7$, $X_8$, and $X_9$ is N and the remaining are each selected from $C(R_7)$.

In some embodiments, $X_5$ is N and $X_6$, $X_7$, $X_8$, and $X_9$ are each selected from $C(R_7)$.

In some embodiments, $X_6$ is N and $X_5$, $X_7$, $X_8$, and $X_9$ are each selected from $C(R_7)$.

In some embodiments, $X_7$ is N and $X_5$, $X_6$, $X_8$, and $X_9$ are each selected from $C(R_7)$.

In some embodiments, $X_8$ is N and $X_5$, $X_6$, $X_7$, and $X_9$ are each selected from $C(R_7)$.

In some embodiments, $X_9$ is N and $X_5$, $X_6$, $X_7$, and $X_8$ are each selected from $C(R_7)$.

In some embodiments, $X_5$, $X_6$, $X_7$, $X_8$, and $X_9$ are each CH.

In some embodiments, $X_6$, $X_7$, $X_8$, and $X_9$ are each CH, $X_5$ is $C(R_7)$, and $R_7$ is selected from halogen atom, $C_1$-$C_6$ alkyl, $C_1$-$C_6$ alkoxy, and halogenated $C_1$-$C_6$ alkyl.

In some embodiments, $X_5$, $X_7$, $X_8$, and $X_9$ are each CH, $X_6$ is $C(R_7)$, and $R_7$ is selected from halogen atom, $C_1$-$C_6$ alkyl, $C_1$-$C_6$ alkoxy, and halogenated $C_1$-$C_6$ alkyl.

In some embodiments, $X_5$, $X_6$, $X_8$, and $X_9$ are each CH, $X_7$ is $C(R_7)$, and $R_7$ is selected from halogen atom, $C_1$-$C_6$ alkyl, $C_1$-$C_6$ alkoxy, and halogenated $C_1$-$C_6$ alkyl.

In some embodiments, $X_5$, $X_6$, $X_7$, and $X_9$ are each CH, $X_8$ is $C(R_7)$, and $R_7$ is selected from halogen atom, $C_1$-$C_6$ alkyl, $C_1$-$C_6$ alkoxy, and halogenated $C_1$-$C_6$ alkyl.

In some embodiments, $X_5$, $X_6$, $X_7$, and $X_8$ are each CH, $X_9$, is $C(R_7)$, and $R_7$ is selected from halogen atom, $C_1$-$C_6$ alkyl, $C_1$-$C_6$ alkoxy, and halogenated $C_1$-$C_6$ alkyl.

In some embodiments, W is selected from O, $N(R_6)$, or S, $R_6$ is selected from H or $C_1$-$C_6$ alkyl; Y is selected from $C_1$-$C_6$ alkylene.

In some embodiments, Y is selected from $C_1$-$C_3$ alkylene, such as methylene, 1,1-ethylidene, and 1,2-ethylidene.

In some embodiments, n is 1 or 2.

In some embodiments, n is 1.

In some embodiments, a chiral carbon atom in

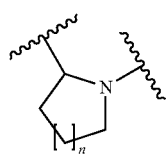

is of a sinister configuration.

In some embodiments, $R_1$ is selected from the following groups:

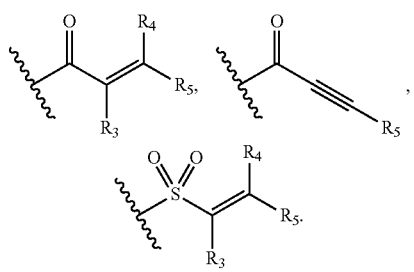

In some embodiments, $R_1$ is selected from

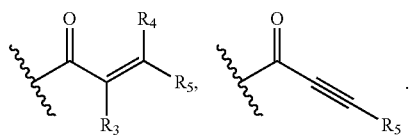

In some embodiments, $R_5$ is selected from H, $C_1$-$C_6$ alkyl, $C_3$-$C_6$ cycloalkyl, $C_1$-$C_4$ alkyl substituted with $C_1$-$C_3$ alkoxy, $C_1$-$C_4$ alkyl substituted with $C_1$-$C_3$ alkyl amino, $C_1$-$C_4$ alkyl substituted with di($C_1$-$C_3$ alkyl) amino, and $C_1$-$C_4$ alkyl substituted with 5 to 6 membered saturated nitrogen-contaning heterocyclic group.

In some embodiments, $R_1$ is

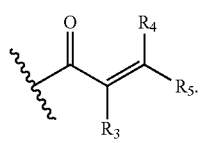

In some embodiments, $R_3$ is H.

In some embodiments, $R_4$ is H.

In some embodiments, $R_5$ is selected from H, $C_1$-$C_4$ alkyl substituted with $C_1$-$C_3$ alkoxy, $C_1$-$C_4$ alkyl substituted with $C_1$-$C_3$ alkyl amino, $C_1$-$C_4$ alkyl substituted with di($C_1$-$C_3$ alkyl) amino, and $C_1$-$C_4$ alkyl substituted with 5 to 6 membered saturated nitrogen-contaning heterocyclic group.

In some embodiments, $R_1$ is

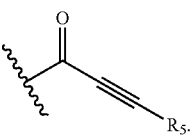

In some embodiments, $R_5$ is selected from H, $C_1$-$C_4$ alkyl, and $C_3$-$C_6$ cycloalkyl.

In some embodiments, A is CH;

$X_1$, $X_2$, $X_3$, and $X_4$ are each CH; or $X_1$ is N, $X_2$, $X_3$, and $X_4$ are each CH; or $X_2$ is N, $X_1$, $X_3$, and $X_4$ are each CH; or $X_3$ is N, $X_1$, $X_2$, and $X_4$ are each CH, or $X_4$ is N, $X_1$, $X_2$, and $X_3$ are each CH;

W is O, $N(R_6)$, or S, $R_6$ is selected from H or $C_1$-$C_3$

Y is selected from $C_1$-$C_3$ alkylene;

n is 1;

$R_1$ is selected from

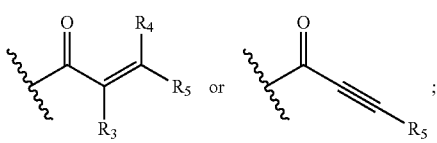

wherein $R_3$ is H;

$R_4$ is H;

$R_5$ is selected from H, $C_1$-$C_6$ alkyl, $C_3$-$C_6$ cycloalkyl, $C_1$-$C_4$ alkyl substituted with $C_1$-$C_3$ alkoxy, $C_1$-$C_4$ alkyl substituted with $C_1$-$C_3$ alkyl amino, $C_1$-$C_4$ alkyl substituted with di($C_1$-$C_3$ alkyl) amino, and $C_1$-$C_4$ alkyl substituted with 5 to 6 membered saturated nitrogen-contaning heterocyclic group;

Ar is selected from phenyl or 6 membered nitrogen-containing heteroaryl, optionally, the phenyl or 6 membered nitrogen-containing heteroaryl is substituted with a group selected from halogen atom, $C_1$-$C_6$ alkyl, $C_1$-$C_6$ alkoxy, and halogenated $C_1$-$C_6$ alkyl.

In some embodiments, the compound has a structure as represented by formula (III):

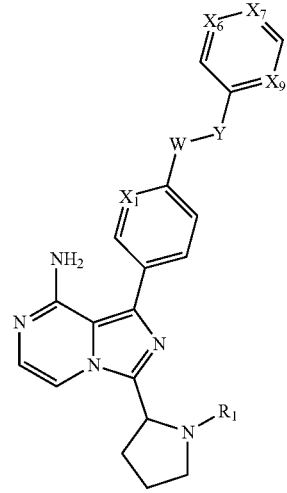

(III)

wherein $X_1$ is CH or N;
W is selected from O, S, and $N(R_6)$, $R_6$ is selected from H or methyl;
Y is selected from methylene, 1,1-ethylidene, and 1,2-ethylidene;
$X_6$ and $X_7$ are each independently selected from $C(R_7)$, $R_7$ is selected from H, F, trifluoromethyl, and methoxyl.
$X_9$ is selected from CH or N;
$R_1$ is

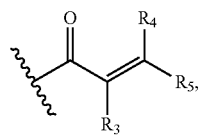

wherein $R_3$ is H, $R_4$ is H, and $R_5$ is selected from H, methyl substituted with methoxyl, methyl substituted with dimethyl amino, and methyl substituted with piperidyl; or
$R_1$ is

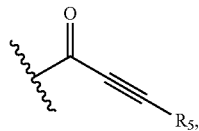

wherein $R_5$ is selected from H, methyl, ethyl, isopropyl, and cyclopropyl; or
$R_1$ is

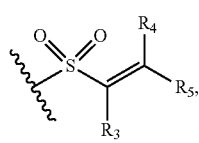

wherein $R_3$, $R_4$, and $R_5$ are each H.

In some embodiments, the compound of the present disclosure is selected from:

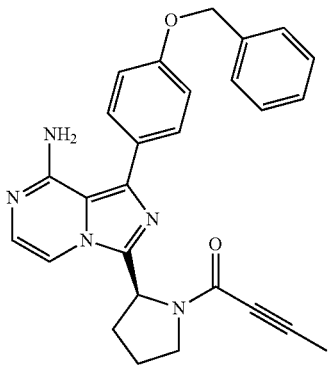

compound 1

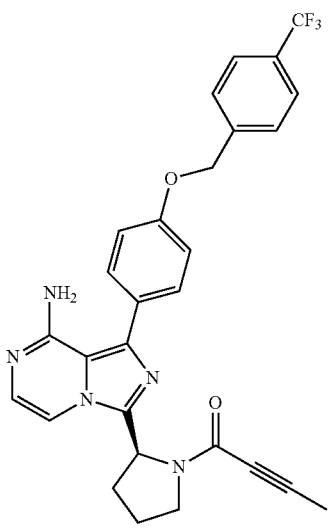

compound 2

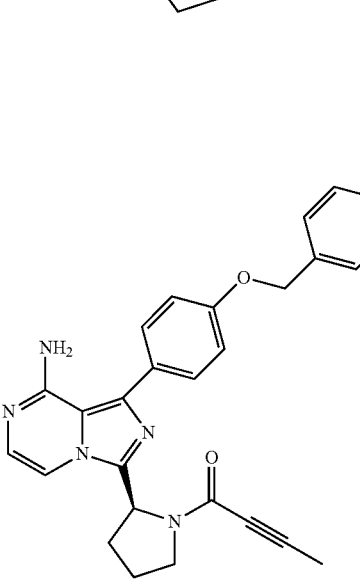

compound 3 compound 4
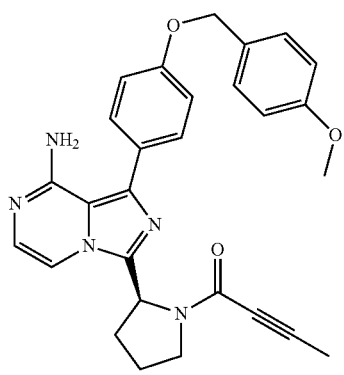
compound 5
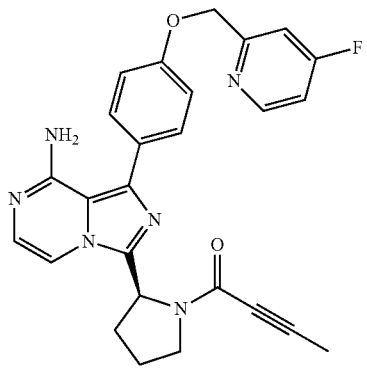
compound 6
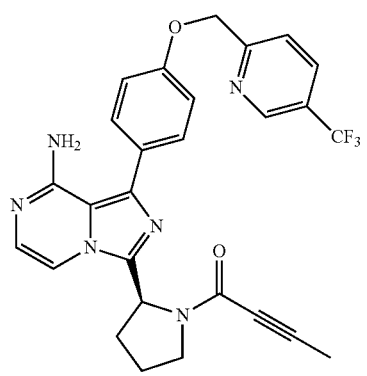
compound 7
compound 8
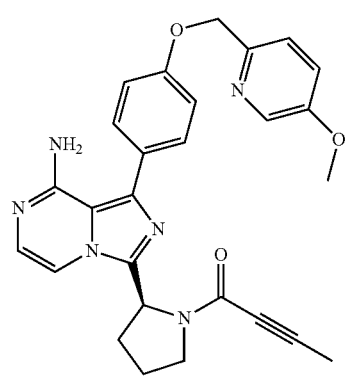
compound 9
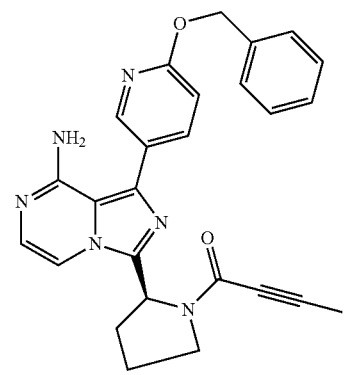
compound 10
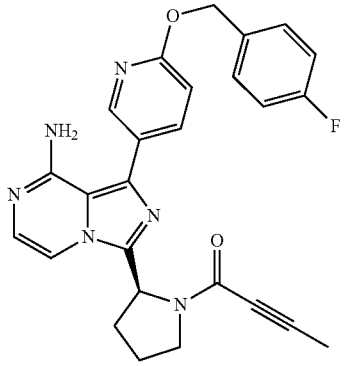
compound 11
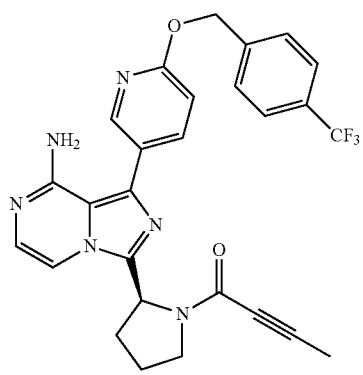

compound 12
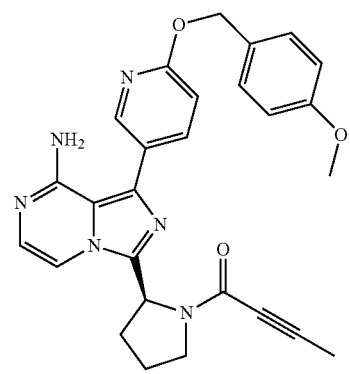
compound 13
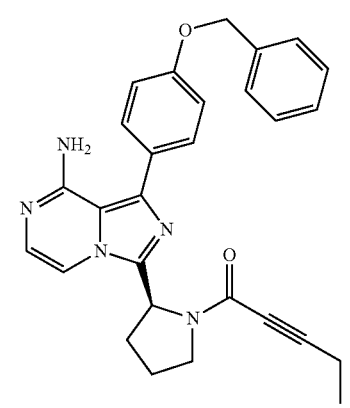
compound 14
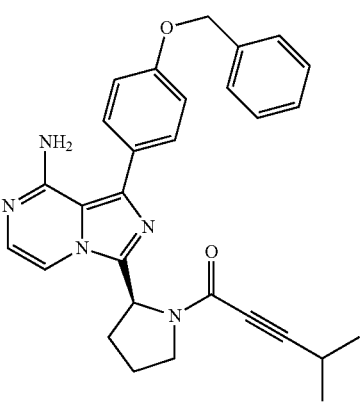
compound 15
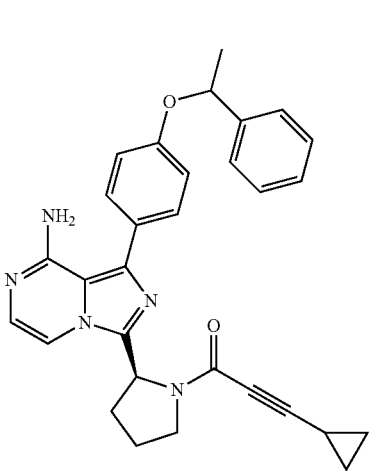
compound 16
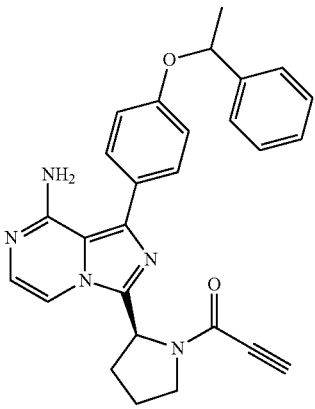
compound 17
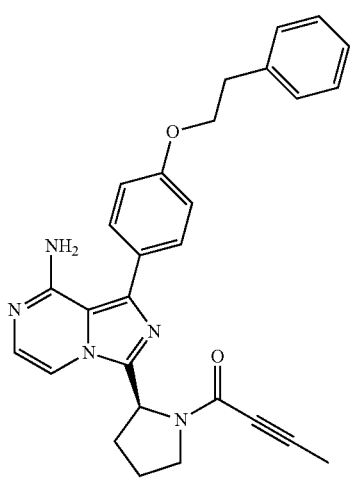
compound 18
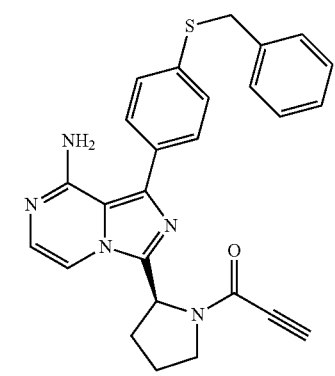
compound 19
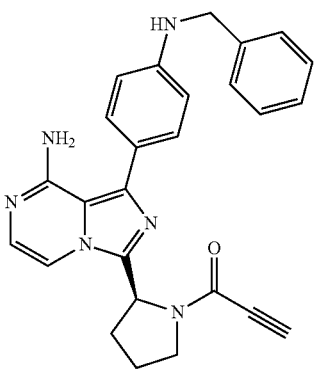

compound 20
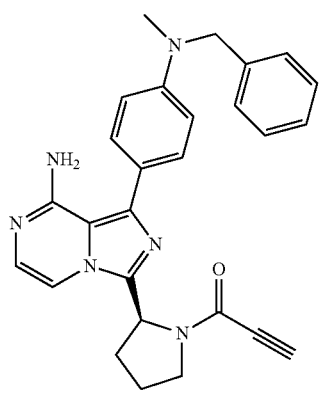
compound 21
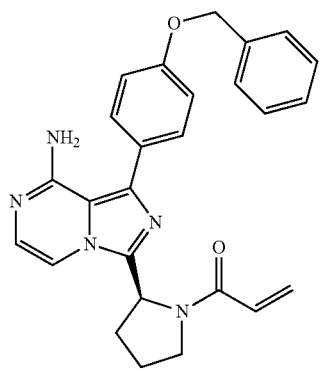
compound 22
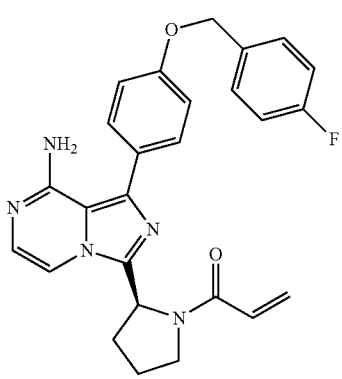
compound 23
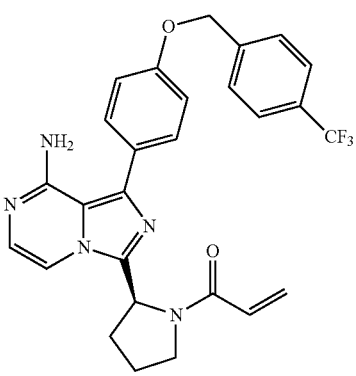
compound 24
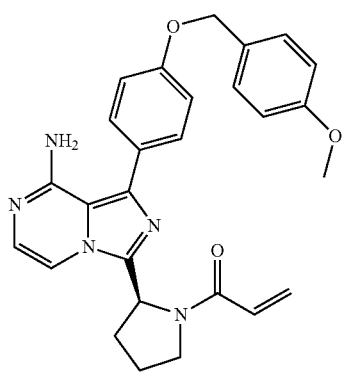
compound 25
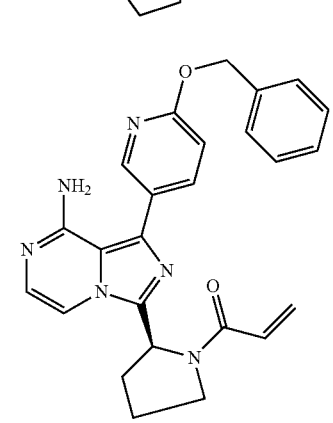
compound 26
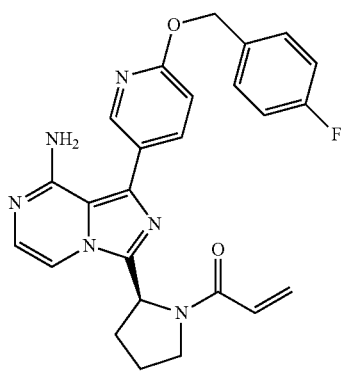
compound 27
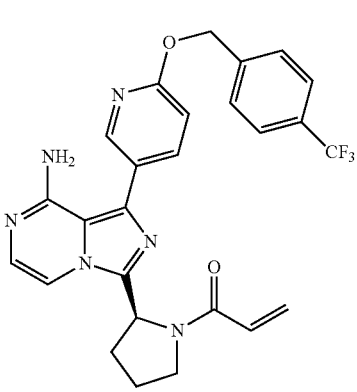

compound 28
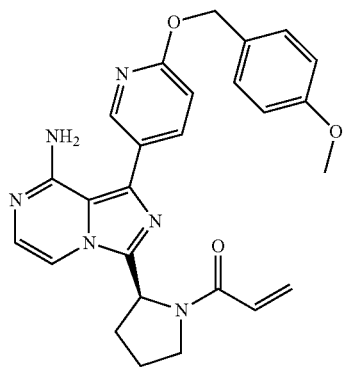
compound 29
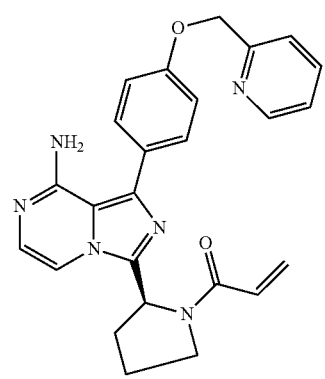
compound 30
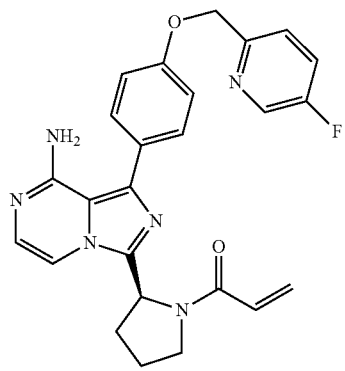
compound 31
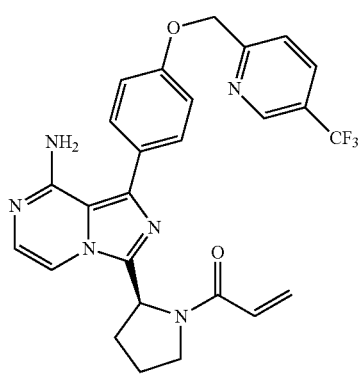
compound 32
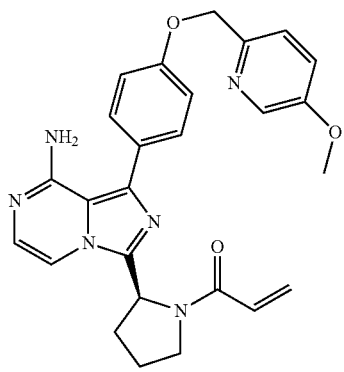
compound 33
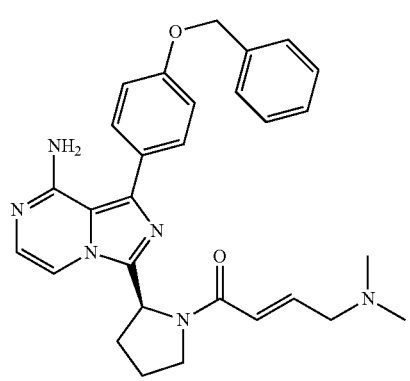
compound 34
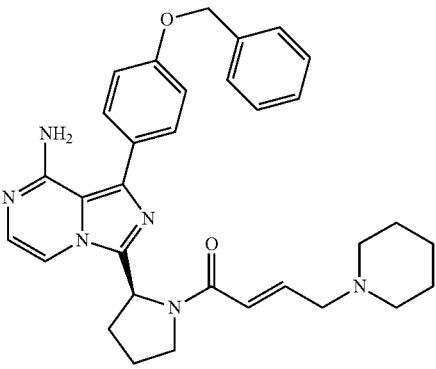
compound 35
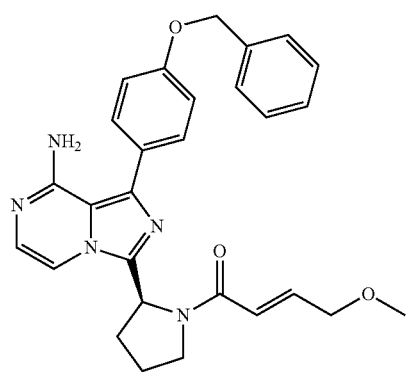

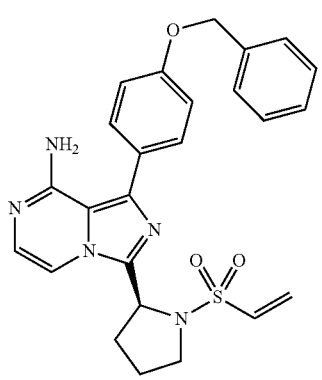

compound 36

One aspect of the present disclosure relates to a pharmaceutical composition including the compound of the present disclosure, the pharmaceutically acceptable salt thereof, the stereoisomer thereof, or the prodrug thereof.

Optionally, the pharmaceutical composition of the present disclosure further includes one or more of pharmaceutical excipients.

In the present disclosure, the pharmaceutical excipient is a vehicle or an additive used in pharmaceutical production and prescription dispensing and refers to a material, except for an active component, which has been rationally evaluated in safety, contained in a pharmaceutical preparation. In addition to formability, serving as a carrier, and improving stability, the pharmaceutical excipient further has important functions such as solubilization, hydrotropy, and controlled release and is an important component that may affect the quality, the safety, and the effectiveness of a drug. According to its source, the pharmaceutical excipient can be classified into a natural material, a semisynthetic material, and a synthetic material. According to its effect and use, the pharmaceutical excipient can be classified into a solvent, a propellant, a solubilizer, a hydrotropy agent, an emulsifying agent, a colorant, a binder, a disintegrant, a filler, a lubricant, a wetting agent, an osmotic pressure regulator, a stabilizer, a glidant, a flavoring agent, a preservative, a suspending agent, a coating material, an aromatic, an anti-adhesive agent, an antioxidant, a chelating agent, a penetration enhancer, a pH adjuster, a buffer, a plasticizer, a surfactant, a foaming agent, a defoamer, a thickener, an inclusion agent, a moisturizer, a absorbent, a diluent, a flocculant and deflocculant, a filter aid, a release retardant, and so on. Accoding to its administration manner, the pharmaceutical excipient can be classified into oral administration, injection administration, mucosa administration, percutaneous or topical administration, inhalation administration via nasal cavity or oral cavity, ophthalmic administration, and so on. The same pharmaceutical excipient can be used for pharmaceutical preparations having different administration manners and can have different effects and uses.

The pharmaceutical composition of the present disclosure can be made into various suitable dosage forms according to its administration manner.

In oral administration, the pharmaceutical composition can be made into any acceptable preparation forms for oral administration, including but not being limited to tablet, capsule, granule, pill, syrup, oral solution, oral suspension, oral emulsion, and so on. Wherein, a carrier used by the tablet is generally comprised of lactose and maize starch and can be further added with a lubricant such as magnesium stearate. A diluent used by the capsule is generally comprised of lactose and dry maize starch. An active component is generally mixed with a suitable emulsifying agent and a suitable suspending agent in the oral suspension. Optionally, a sweetening agent, an aromatic agent, and a colorant can be further added into the above oral preparation forms.

In percutaneous or topical administration, the pharmaceutical composition can be made into suitable ointment form, lotion form, and liniment form, wherein an active component can be suspended or dissolved into one or more of carries. A carrier useable in the ointment preparation includes but is not limited to mineral oil, liquid vaseline, white vaseline, propylene glycol, polyethylene oxide, polypropylene oxide, emulsified wax, and water. A carrier useable in the lotion or liniment preparation includes but is not limited to mineral oil, dehydrated sorbitan monostearate, Tween 60, hexadecyl ester wax, hexadecene aromatic alcohol, 2-octyldodecanol, benzyl alcohol, and water.

The pharmaceutical composition can also be administered in form of injection, including injection solution, sterile powder for injection, and concentrated solution for injection. Wherein, a usable carrier and a usable solvent include water, Ringer's solution, and isotonic sodium chloride solution. In addition, a sterile nonvolatile oil, such as monoglyceride and diglyceride, can also be used as a solvent or a suspending medium.

Optionally, the compound of the present disclosure, the pharmaceutically acceptable salt thereof, the stereoisomer thereof, or the prodrug thereof can be administered in combination with a second therapeutic agent. Therefore, the pharmaceutical composition of the present disclosure can optionally include one or more second therapeutic agents. In some embodiments, the second therapeutic agent is a chemotherapeutic drug, a targeting anticancer drug, or an immunotherapeutic drug. In some embodiments, the second therapeutic agent is selected from rituximab, lenalidomide, fludarabine, cyclophosphamide, adriamycin, vincristine, and prednisone.

One aspect of the present disclosure relates to a use of the compound, the pharmaceutically acceptable salt thereof, the stereoisomer thereof, or the prodrug thereof for preparing a drug. The drug is used for preventing and/or treating a disease and/or a condition of a subject associated with overactivity of Bruton's tyrosine kinase.

In some embodiments, the disease and/or the condition associated with overactivity of Bruton's tyrosine kinase is selected from tumor (such as hematological tumor or solid tumor), inflammation, or autoimmune disease.

In some embodiments, the hematological tumor is selected from lymphoma, myeloma, lymphocytic leukemia, and acute myeloid leukemia.

In some embodiments, the solid tumor is selected from lung cancer, breast cancer, prostate cancer, stomach cancer, liver cancer, pancreatic cancer, ovarian cancer, and colon cancer.

In some embodiments, the inflammation or autoimmune disease is selected from rheumatoid arthritis, lupus erythematosus, lupus nephritis, multiple sclerosis, Sjogren's syndrome, and underlying disease asthma.

In some embodiments, the subject is a mammal; such as a bovine, an equine, an ovine, a porcine, a canine, a feline, a rodent, and a primate; such as a human being.

In some embodiments, the pharmaceutical composition further includes one or more second therapeutic agents. In some embodiments, the second therapeutic agent is a chemotherapeutic drug, a targeting anticancer drug, or an immunotherapeut c drug. In some embodiments, the second therapeutic agent is selected from rituximab, lenalidomide, fludarabine, cyclophosphamide, adriamycin, vincristine, and prednisone.

One aspect of the present disclosure relates to a method for preventing and/or treating a disease and/or a condition of a subject associated with overactivity of Bruton's tyrosine kinase. The method includes administering the subject with a preventively and/or therapeutically effective amount of the compound of the present disclosure, the pharmaceutically acceptable salt thereof, the stereoisomer thereof, or the prodrug thereof or the pharmaceutical composition of the present disclosure.

In some embodiments, the disease and/or the condition associated with overactivity of Bruton's tyrosine kinase is selected from tumor (such as hematological tumor or solid tumor), inflammation, or autoimmune disease.

In some embodiments, the hematological tumor is selected from lymphoma, myeloma, lymphocytic leukemia, and acute myeloid leukemia.

In some embodiments, the solid tumor is selected from lung cancer, breast cancer, prostate cancer, stomach cancer, liver cancer, pancreatic cancer, ovarian cancer, and colon cancer.

In some embodiments, the inflammation or autoimmune disease is selected from rheumatoid arthritis, lupus erythematosus, lupus nephritis, multiple sclerosis, Sjogren's syndrome, and underlying disease asthma.

In some embodiments, the subject is a mammal; such as a bovine, an equine, an ovine, a porcine, a canine, a feline, a rodent, and a primate; such as a human being.

In some embodiments, the method further includes administering the subject with one or more second therapeutic agents. In some embodiments, the second therapeutic agent is a chemotherapeutic drug, a targeting anticancer drug, or an immunotherapeutic drug. In some embodiments, the second therapeutic agent is selected from rituximab, lenalidomide, fludarabine, cyclophosphamide, adriamycin, vincristine, and prednisone.

Another aspect of the present disclosure relates to a use of the compound of the present disclosure, the pharmaceutically acceptable salt thereof, the stereoisomer thereof, or the prodrug thereof for preparing a preparation, and the preparation is used for decreasing or inhibiting an activity of Bruton's tyrosine kinase in a cell.

In some embodiments, the preparation is administered into a body of a subject (such as a mammal; such as a bovine, an equine, an ovine, a porcine, a canine, a feline, a rodent, and a primate; such as a human being) to decrease or inhibit the activity of Bruton's tyrosine kinase in a cell in vivo; or the preparation is administered to a cell in vitro (such as a cell line or a cell from the subject) to decrease or inhibit the activity of Bruton's tyrosine kinase in the cell in vitro.

In some embodiments, the cell is selected from a tumor cell, such as a solid tumor cell, such as a lung cancer cell, a breast cancer cell, a prostate cancer cell, a stomach cancer cell, a liver cancer cell, a pancreatic cancer cell, an ovarian cancer cell, and a colon cancer cell.

In some embodiments, the cell is selected from a myeloid cell or a lymphocyte.

In some embodiments, the cell is a primary cell from the subject, a culture of the primary cell, or an established cell line.

Another aspect of the present disclosure relates to a method for decreasing or inhibiting an activity of Bruton's tyrosine kinase in a cell, including administering the cell with an effective amount of the compound of the present disclosure, the pharmaceutically acceptable salt thereof, the stereoisomer thereof, or the prodrug thereof.

In some embodiments, the method is performed in vivo or in vitro. Preferably, the method is performed in vivo, for example, the method is applied in a body of a subject (such as a mammal; such as a bovine, an equine, an ovine, a porcine, a canine, a feline, a rodent, and a primate; such as a human being) to decrease or inhibit the activity of Bruton's tyrosine kinase in a cell in vivo; or the method is performed in vitro, for example, the method is applied in a cell in vitro (such as a cell line or a cell from the subject) to decrease or inhibit the activity of Bruton's tyrosine kinase in the cell in vitro.

In some embodiments, the cell is selected from a tumor cell, for example, a solid tumor cell, such as a lung cancer cell, a breast cancer cell, a prostate cancer cell, a stomach cancer cell, a liver cancer cell, a pancreatic cancer cell, an ovarian cancer cell, and a colon cancer cell.

In some embodiments, the cell is selected from a myeloid cell or a lymphocyte.

In some embodiments, the cell is a primary cell from the subject, a culture of the primary cell, or an established cell line. Another aspect of the present disclosure relates to a kit including the compound of the present disclosure, the pharmaceutically acceptable salt thereof, the stereoisomer thereof, or the prodrug thereof and optionally further including an instruction for use.

In some embodiments, the kit is used for decreasing or inhibiting an activity of Bruton's tyrosine kinase in a cell.

In some embodiments, the cell is selected from a tumor cell, for example, a solid tumor cell, such as a lung cancer cell, a breast cancer cell, a prostate cancer cell, a stomach cancer cell, a liver cancer cell, a pancreatic cancer cell, an ovarian cancer cell, and a colon cancer cell.

In some embodiments, the cell is selected from a myeloid cell or a lymphocyte.

In some embodiments, the cell is a primary cell from a subject, a culture of the primary cell, or an established cell line.

In the present disclosure, scientific and technical terms used herein have the same meaning as commonly understood by those skilled in the art, unless otherwise indicated. Moreover, cell culture and immunology laboratory procedures used herein are all conventional procedures widely used in the related field. At the same time, to better understand the present disclosure, definitions and explanations of relevant terms are provided below.

As used herein, the term "stereoisomer" includes conformational isomer and configurational isomer, wherein the configurational isomer mainly includes cis-trans-isomer and optical isomer. The compound of the present disclosure may be present in stereoisomer form and thus covers all possible stereoisomer forms and any combination or mixture thereof, for example, individual enantiomer, individual diastereoisomer, or mixture of the above. When the compound of the present disclosure contains an olefinic double bond, unless specifically indicated, the compound includes cis-isomer, trans-isomer, and any combination thereof.

As used herein, the term "pharmaceutically acceptable salt" refers to: (1) a salt formed by an acidic functional group (such as —COOH, —OH, —SO$_3$H, and the like) existing in the compound of the present disclosure and a suitable inorganic or organic positive ion (base), for example, a salt formed by the compound of the present disclosure and an alkali or alkaline-earth metal, an ammonium salt of the compound of the present disclosure, and a salt formed by the compound of the present disclosure and a nitrogen-containing organic base; and (2) a salt formed by an alkaline functional group (such as —NH$_2$ and the like) existing in the compound of the present disclosure and a suitable inorganic or organic negative ion (acid), for example, a salt formed by the compound of the present disclosure and an inorganic acid or organic carboxylic acid.

Therefore, the "pharmaceutically acceptable salt" of the compound of the present disclosure includes, but is not limited to, alkali metal salt, such as sodium salt, potassium salt, lithium salt, etc.; alkaline earth metal salt, such as calcium salt, magnesium salt, etc.; other metal salt, such as aluminum salt, iron salt, zinc salt, copper salt, nickel salt, cobalt salt, etc.; inorganic alkali salt, such as ammonium salt; organic alkali salt, such as tert-octylamine salt, dibenzylamine salt, morpholine salt, glucosamine salt, phenylglycine alkyl ester salt, ethanediamine salt, N-methylglucosamine salt, guanidine salt, diethylamine salt, triethylamine salt, di cyclohexylamine salt, N,N'-dibenzylethanediamine salt, chloroprocaine salt, procaine salt, dietha-.nol amine salt, N-benzyl-phenylethylamine salt, piperazine salt, tetramethylammonium salt, tri(hydroxymethyl)methylammonium salt; haloid acid salt, such as hydrofluoride, hydrochloride, hydrobromide, hydriodide, etc.; inorganic acid salt, such as nitrate, perchlorate, sulfate, phosphate, etc.; low-alkyl sulfonate, such as, methyl sulfonate, trifluoromethyl sulfonate, ethyl sulfonate, etc.; aryl sulfonate, such as benzene sulfonate, p-benzene sulfonate, etc.; organic acid salt, such as acetate, malate, fumarate, succinate, citrate, tartrate, oxalate, maleate, etc; amino acid salt, such as glycine salt, trimethyl glycine salt, arginine salt, ornithine salt, glutamine salt, aspartates, etc.

As used herein, the term "prodrug", also known as precursor drug, drug precursor, pro-drug, refers to a compound, obtained by modifying the compound of the present disclosure, having no or less activity in vitro and releasing an active drug in vivo via enzymatic or non-enzymatic conversion to play a therapeutic effect. The design principle and preparation method of the prodrug is known to those skilled in the art. As used herein, the term "$C_1$-$C_6$ alkyl" refers to straight or branched alkyl containing 1 to 6 carbon atoms, such as $C_1$-$C_5$ alkyl, $C_1$-$C_4$ alkyl, $C_1$-$C_3$ alkyl, $C_1$-$C_2$ alkyl, $C_1$ alkyl, $C_2$ alkyl, $C_3$ alkyl, $C_4$ alkyl, $C_5$ alkyl, or $C_6$ alkyl. The specific example includes, but not limited to, methyl, ethyl, n-propyl, iso-propyl, n-butyl, iso-butyl, sec-butyl, tert-butyl, n-pentyl, iso-pentyl, 2-methylbutyl, neo-pentyl, 1-ethylpropyl, n-hexyl, iso-hexyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl, 2-ethylbutyl, 1,2-dimethylpropyl. The term "$C_1$-$C_4$ alkyl" refers to specific examples containing 1 to 4 carbon atoms in $C_1$-$C_6$ alkyl. The term "$C_1$-$C_3$ alkyl" refers to specific example containing 1 to 3 carbon atoms in $C_1$-$C_6$ alkyl.

As used herein, the term "$C_1$-$C_6$ alkoxy" refers to a group formed by way of "$C_1$-$C_6$ alkyl-O-", wherein "$C_1$-$C_6$ alkyl" is as defined above. The specific example includes, but not limited to, methoxy, ethoxy, n-propoxy, iso-propoxy, n-butoxy, 2-butoxy, iso-butoxy, test-butoxy, sec-butoxy, pentyloxy, hexoxy, and so on. The term "$C_1$-$C_3$ alkoxy" refers to specific example containing 1 to 3 carbon atoms in $C_1$-$C_6$ alkoxy.

As used herein, the term "halogen atom" refers to fluorine atom, chlorine atom, bromine atom, and iodine atom.

As used herein, the term "halogenated $C_1$-$C_6$ alkyl" refers to a group derived from "$C_1$-$C_6$ alkyl" in which one or more hydrogen atoms are substituted by one or more halogen atoms, and the terms "halogen atom" and "$C_1$-$C_6$ alkyl" are as defined above. The term "halogenated $C_1$-$C_4$ alkyl" of the present disclosure refers to specific example containing 1 to 4 carbon atoms in halogenated $C_1$-$C_6$ alkyl.

As used herein, the term "$C_1$-$C_3$ alkyl amino" refers to a group formed by way of "$C_1$-$C_3$ alkyl-NH-", wherein "$C_1$-$C_3$ alkyl" is as defined above. The specific example includes, but not limited to, tnethylatnino, ethylamino, propylamino, and isopropylatnino.

As used herein, the term "di($C_1$-$C_3$ alkyl) amino" refers to a group formed by way of "di($C_1$-$C_3$ alkyl)-N", wherein "$C_1$-$C_3$ alkyl" is as defined above. The specific example includes, but not limited to, dimethylamino, diethylamino, dipropylamino, methylethylamino, and so on.

As used herein, the term "$C_1$-$C_6$ alkylene" refers to a group derived from $C_1$-$C_6$ alkyl by removing one hydrogen atom, such as $C_1$-$C_3$ alkylene, $C_1$-$C_4$ alkylene, $C_2$-$C_4$ alkylene, wherein "$C_1$-$C_6$ alkyl" is as defined above. The specific example includes, but not limited to, methylene (—CH$_2$—), 1,2-ethylidene (—CH$_2$CH$_2$—), 1,1-ethylidene (—CH(CH$_3$H, trimethylene (—CH$_2$CH$_2$CH$_2$—), and so on. The "$C_1$-$C_3$ alkylene" refers to specific example containing 1 to 3 carbon atoms in above examples.

As used herein, the term "heterocyclic group" refers a cyclic group in which at least one of ring atoms is a heteroatom (such as oxygen atom, sulphur atom, nitrogen atom), such as 3 to 8-membered heterocyclic group, 5 to 6 membered heterocyclic group, nitrogen-containing heterocyclic group, oxygen-containing heterocyclic group, sulphur-containing heterocyclic group, saturated heterocyclic group, unsaturated heterocyclic group, 3 to 8 membered saturated heterocyclic group, 5 to 6 membered saturated heterocyclic group, 3 to 8 membered nitrogen-containing heterocyclic group, 3 to 8-membered oxygen-containing heterocyclic group, 3 to 8 membered sulphur-containing heterocyclic group, 5 to 6 membered nitrogen-containing heterocyclic group, 3 to 8 membered saturated nitrogen-containing heterocyclic group, 5 to 6 membered saturated nitrogen-containing heterocyclic group. The specific example includes, but not limited to, aziridinyl, 2H-aziridinyl, diazacyclopropyl, 3H-diazacyclopropenyl, azetidinyl, 1,4-dioxanyl, 1,3-dioxanyl, 1,3-dioxacyclop , 1,4-dioxacyclohexadienyl, tetrahydrofuranyl, dihydropyrrolyl, pyrrolidinylyl, imidazolidinyl, 4,5-dihydroimidazolyl, pyrazolidinyl, 4,5-dihydropyrazotyl, 2,5-dihydrothienyl, tetrahydrothienyl, 4,5-dihydrothiazolyll, piperidyl, piperazinyl, morpholinyl, hexahydropyrimidyl, hexahydropyridazinyl, 4,5-dihydrooxazolyl, 4,5-dihydroisoxazollyl, 2,3-dihydroisoxazolyl, 2H-1,2-oxazinyl, 4F1-1,2-oxazinyl, 6H-1,2-oxazinyl, 4H-1,3-oxazinyl, 6H-1,3-oxazinyl, 4H-1,4-oxazinyl, 4H-1,3-thiazinvi, 6H-1,3-thiazinyl, 2H-pyranyl, 2H-pyran-2-one, 3,4-dihydro-2H-pyranyl, and so on.

As used herein, the term "aryl" refers to aromatic monocyclic or polycyclic hydrocarbyl, such as 6 to 10 membered aryl. The specific example includes, but not limited to, phenyl, naphthyl, anthracenyl, phenanthryl, and so on.

As used herein, the term "heteroaryl" refers to aryl containing at least one heteroatom selected from nitrogen, oxygen, and sulfur, such as 6 to 10 membered heteroaryl, 5 to 6 membered heteroaryl, nitrogen-containing heteroaryl, oxygen-containing heteroaryl, sulfur-containing heteroaryl, 5 to 6 membered oxygen-containing heteroaryl, and 6 to 10 membered oxygen-containing heteroaryl. The specific example includes, but not limited to, furanyl, thienyl, pyrrolyl, thiazolyl, isothiazolyl, thiadiazolyl, oxazolyl, isoxazolyl, imidazolyl pyrazolyl, 1,2,3-triazolyl, 1,2,4-triazolyl, 1,2,3-oxadiazolyl, 1,2,4-oxadiazolyl, 1,2,5-oxadiazolyl, 1,3, 4-oxadiazolyl, pyridyl, 2-pyridinone, 4-pyridinone, pyrimidinyl, 2H-1,2-oxazinyl, 4H-1,2-oxazinyl, 6H-1,2-oxazinyl, 4H-1,3 -oxazinyl, 6H-1,3-oxazinyl, 4H-1,4-oxazinyl, pyridazinyl, pyrazinl, 1,2,3-triazinyl, 1,3,5-triazinyl, 1,2,4, 5-tetraazinyl, azacycloheptatriene, 1,3-diazepine, benzofuranyl, benzoisofuranyl benzothienyl, indolyl, isoindolyl, benzoxazolyl, benzimidazolyl, indazolyl, benzotriazolyl, quinolyl, 2-quinolinone, 4-quinolinone, 1-isoquinolinone, isoquinolyl, acridinyl, phenanthridinyl, benzopyridazinyl, pyridazinyl, quinazolinyl, quinoxalinyl, phenazinyl, pteridinyl, purinyl, naphthyridinyl, phenazine, phenothiazine, etc.

As used herein, the term "$C_3$-$C_6$ cycloalkyl" refers to monocyclic saturated alkyl containing 3 to 6 ring atoms, such as 3 to 4 membered cycloalkyl, 3 to 5 membered cycloalkyl, 4 to 6 membered cycloalkyl, 5 to 6membered cycloalkyl, and 3, 4, 6 membered cycloalkyl. The specific example includes, but not limited to, cyclopropyl, cyclobutyl, cyclopentyl, cyclohexyl, etc.

Beneficial effects of the present invention:

The compound of the present disclosure has a significant inhibitory effect on BTK but no significant inhibitory effect on EGFR, Tec, Txk, and ITK. The compound of the present disclosure can inhibit the tumor growth in a dose-dependent manner. The compound of the present disclosure has good selectivity as compared to the first generation BTK inhibitor and has excellent pharmacokinetic property as compared to the second generation BTK inhibitor and is more safe and effective.

The compound of the present disclosure can be used for treating various diseases involved with BTK and has great application value in particular for treatment of hematological tumor, solid tumor, inflammation, and autoimmune disease.

BRIEF DESCRIPTION OF THE DRAWINGS

FIG. 2 shows dose-effect relationship of the inhibition of the compound 1 to the growth of TMD-8 lymphoma cell strain transplanted tumor, wherein FIG. 2A shows a change of the tumor volume of each group of mice and FIG. 2B shows a change of the weight of each group of mice. The result shows that the compound 1 can inhibit the growth of TMD-8 transplanted tumor dose-dependently via oral administration.

DETAILED DESCRIPTION OF THE EMBODIMENTS

Figure 1:
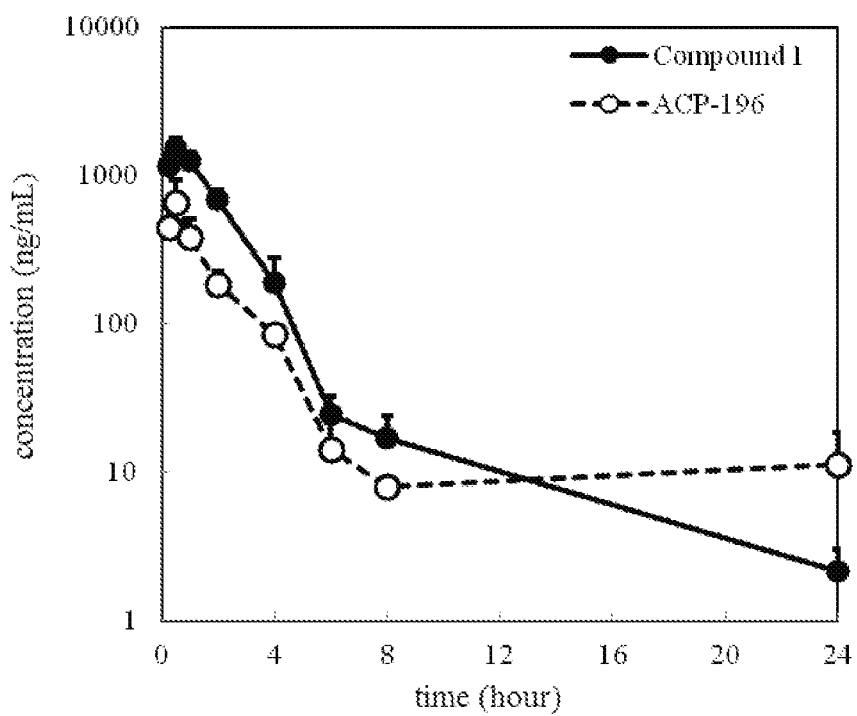
FIG. 1 shows plasma concentration-time curves of rats orally administered respectively with the compound 1 and ACP-196 (20 mg/kg), As shown in the figure, the compound 1 has a shorter half-life and a higher plasma exposure amount.

The embodiments of the present invention will be described in detail below by way of example, however, it should be understood by those skilled in the art that the following examples are intended to illustrate the invention but not to limit the scope of the invention. Where the specific conditions are not indicated in the examples are carried out according to conventional conditions or the conditions recommended by the manufacturer. The reagents or apparatuses, the manufacturers of which are not indicated, are conventional products that are commercially available.

The compound of the present disclosure can be prepared by the following synthetic schemes.

Scheme 1:

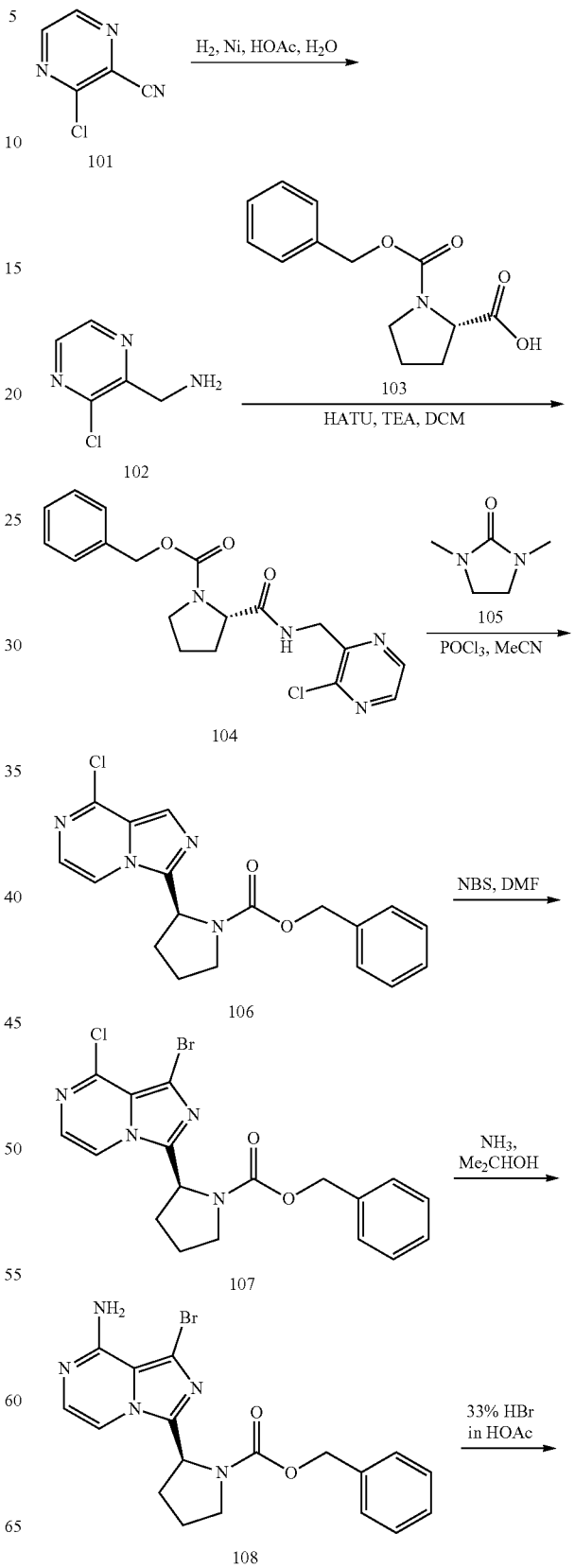

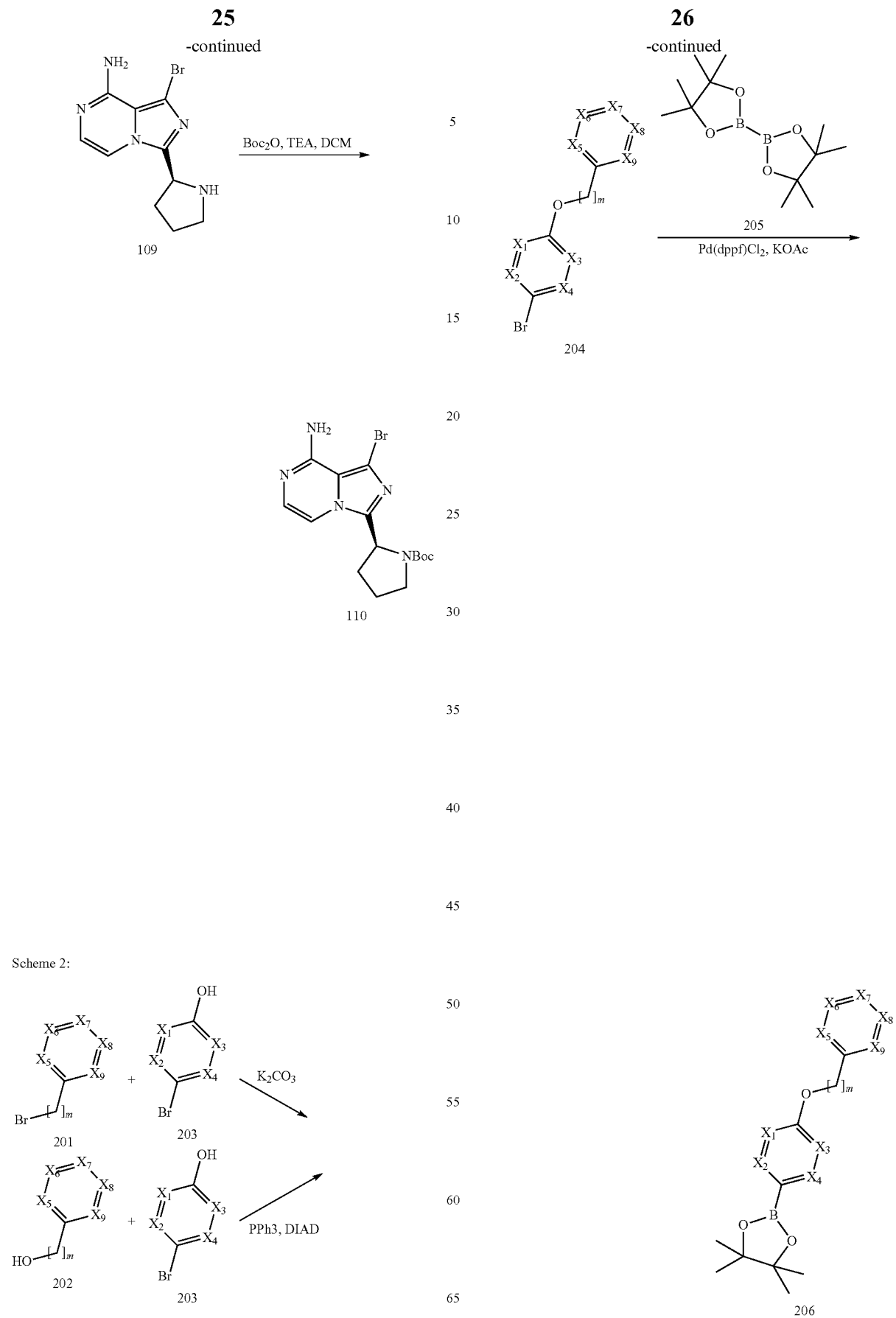
Scheme 2:

Scheme 3:

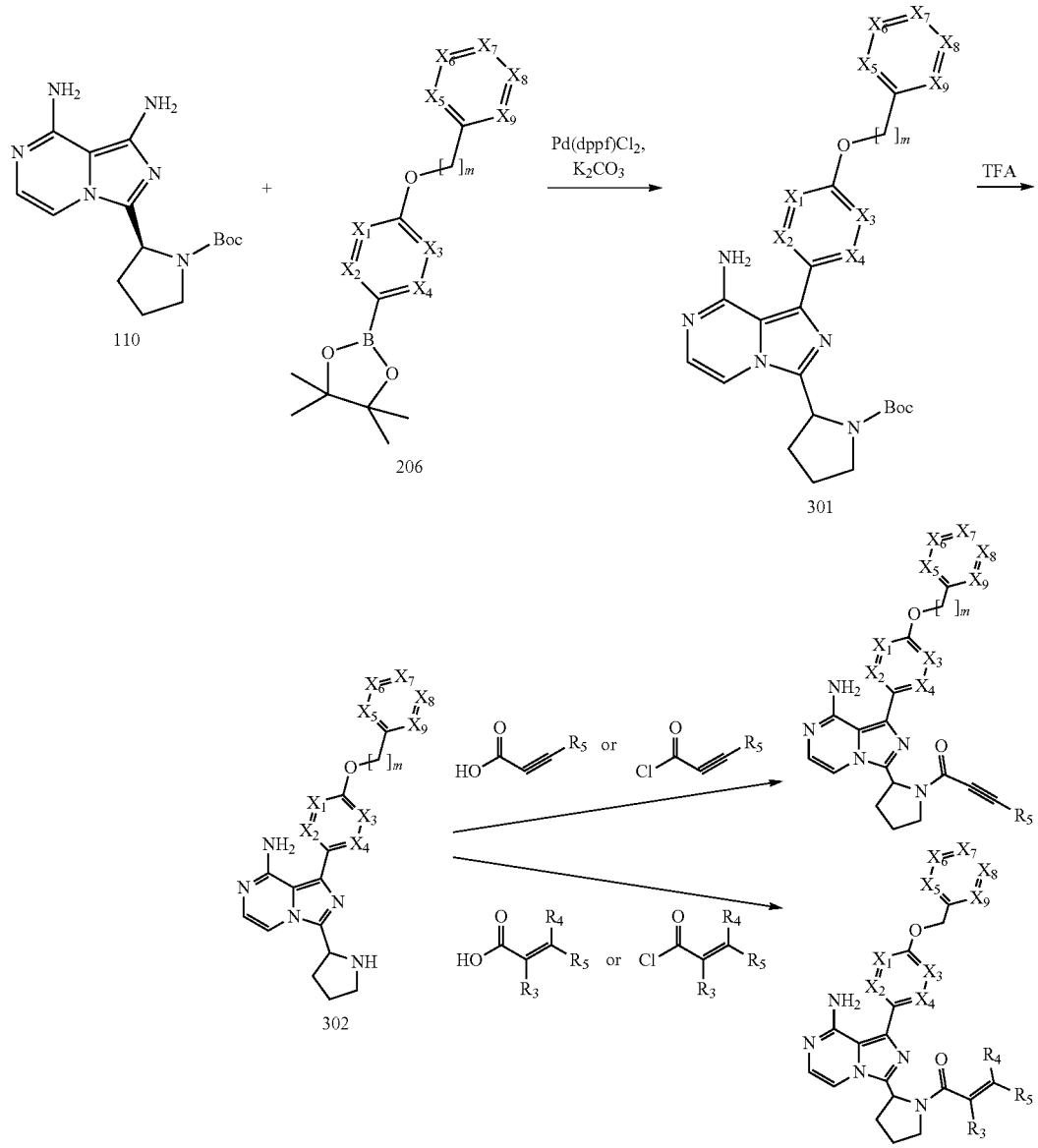

EXAMPLES

Example 1: Preparation of (S)-1-(2-(8-amino-1-(4-(benzyloxy)phenyl)imidazo[1,5-a]pyrazin-3-yl)pyrrolidin-1-yl)but-2-yn-1-one (compound 1)

Step 1a, preparation of (3-chloropyrazin-2-yl)methanamine hydrochloride (compound 102): Raney nickel (4.00 g) was added into a solution of 3-chloropyrazin-2-nitrile (compound 101) (6.00 g, 43.0 mmol, 1.0 equivalent) in acetic acid (50 mL) to react under hydrogen atmosphere at room temperature for 1.5 days. The reaction solution was filtered, the filtrate was spin-dried, the remainder was spun with toluene (40 mL), 1N HCl (15 mL) and toluene (40 mL) successively, the remainder was ultrasonically dissolved in tetrahydrofuran (30 mL) and filtered, the filter cake was spin-dried to obtain (3-chloropyrazin-2-yl)methanamine hydrochloride (8.75 g, yield: 100%). Black solid; LCMS (ESI):m/z 144 [M+1]$^+$.

Step 1b, preparation of benzyl (S)-2-(((3-chloropyrazin-2-yl)methyl)carbamoyl)pyrrolidine-1-carboxylate (compound 104): Triethylamine (5.58 g, 55.2 mmol, 4.0 equivalents) and ((benzyloxy)carbonyl)-L-proline (compound 103) (3.43 g, 13.8 mmol, 1.0 equivalent) were added into a solution of (3-chloropyrazin-2-yl)methanamine hydrochloride (compound 102) (2.48 g, 13.8 mmol, 1.0 equivalent) in dichloromethane (80 mL) at 0° C., stirred for 15 minutes at 0° C., and then 2-(7-azobenzotriazolyl)-N,N,N',N'-tetramethyluronium hexafluorophosphate (HATU, 5.50 g, 14.5 mmol, 1.05 equivalents) was added, and the reaction solution was reacted for 5 minutes at a temperature of 0° C. to room temperature. The reaction solution was diluted with dichloromethane (200 ML) and then washed with ammonium chloride solution (200 mL×1), saturated sodium bicarbonate solution (200 ml×1) and saturated table salt water solution (200 mL×1) successively, the organic phase was dried over anhydrous sodium sulfate and filtered, the filtratewas spin-dried, the remainder was purified by column chromatography (eluent:dichloromethane:methanol=80:1), and benzyl (S)-2-(((3-chloropyrazin-2-yl)methyl)carbamoyl)pyrrolidine-1-carboxylate (2.85 g, yield: 55.1%) was obtained. Light brown oily substance; LCMS(ESI):m/z 375 [M+1]$^+$.

Step 1c, preparation of benzyl (S)-2-(8-chloroimidazo[1,5-a]pyrazin-3-yl)pyrrolidine-1-carboxylate (compound 106): At 0° C., 1,3-dimethylimidazolidinone (compound 105) (2.60 g, 22.8 mmol, 3.0 equivalents) was added into a solution of benzyl (S)-2-(((3-chloropyrazin-2-yl)methyl)carbamoyl)pyrrolidine-1-carboxylate (compound 104) (2.85 g, 7.6 mmol, 1.0 equivalent) in acetonitrile (60 mL), and then phosphorus oxychloride (4.66 g, 30.4 mmol, 4.0 equivalents) was slowly added dropwise, the reaction solution was reacted for 5 minutes at 0° C., recovered to room temperature, and then, under protection of nitrogen, heated to 65° C. and refluxed for 2 days. The reaction solution was slowly poured into ammonia water—ice water (150 mL-300 mL), stirred for 15 minutes, and extracted with ethyl acetate (300 mL×2), the organic phases were combined together and spin-dried, the remainder was purified by column chromatography (eluent:dichloromethane:methanol=500:6), and the benzyl (S)-2-(8-chloroimidazo[1,5-a]pyrazin-3-yl)pyrrolidine-1-carboxylate (2.06 g, yield: 76.3%) was obtained Light brown oily substance, LCMS(ESI):m/z 357 [M+1]$^+$.

Step 1d, preparation of benzyl (S)-2-(1-bromo-8-chloroimidazo[1,5-a]pyrazin-3-yl)pyrrolidine-1-carboxylate (compound 107): N-bromosuccinimide (1.03 g, 5.8 mmol, 1.0 equivalent) was added into a solution of benzyl (S)-2-(8-chloroimidazo[1,5-a]pyrazin-3-yl)pyrrolidine-1-carboxylate (compound 106) (2.06 g, 5.8 mmol, 1.0 equivalent) in N,N-dimethylformamide (24 mL). and the reaction solution was reacted for 3 hours at room temperature. The reaction solution was diluted with ethyl acetate (300 ML) and washed with semi-saturated table salt water solution (300 mL×3), the organic phase was mixed with silica gel and spin-dried, purified by column chromatography (eluent: dichloromethane:methanol=100:1) to obtain benzyl (S)-2-(1-bromo-8-chloroimidazo[1,5-a]pyrazin-3-yl)pyrrolidine-1-carboxylate (1.76 g, yield: 69.6%). Pink solid; LCMS (ESI):m/z 435 [M+1]$^+$.

Step 1e, preparation of benzyl (S)-2-(8-amino-1-bromoimidazo[1,5-a]pyrazin-3-yl)pyrrolidine-1-carboxylate (compound 108): Benzyl (S)-2-(1-bromo-8-chloroimidazo[1,5-a]pyrazin-3-yl)pyrrolidine-1-carboxylate (compound 107) (1.76 g, 4.0 mmol, 1.0 equivalent), isopropanol (30 mL) and ammonia (10 mL) were added into a sealed tube, heated to 110° C. and reacted overnight under the protection of nitrogen. The reaction solution was spin-dried, the remainder was dissolved in methanol and then spin-dried, purified by column chromatography (eluent:dichloromethane:methanol=100:1) to obtain benzyl (S)-2-(8-amino-1-bromoimidazo[1,5-a]pyrazin-3-yl)pyrrolidine-1-carboxylate(1.32 g, yield: 79.5%). White foamy substance; LCMS (ESI); m/z 416 [M+1]$^+$.

Step 1f, preparation of (S)-1-bromo-3-(pyrrolidin-2-yl)imidazo[1,5-a]pyrazin-8-amine hydrobromide (compound 109): Benzyl (S)-2-(8-amino-1-bromoimidazo[1,5-a]pyrazin-3-yl)pyrrolidine-1-carboxylate (compound 108) (1.32 g, 3.2 mmol, 1.0 equivalent) and a 33% solution of hydrobromic acid in acetic acid (12 mL) were added into a reaction vessel, ultrasonically dissolved, and reacted for 20 minutes at room temperature. The reaction solution was poured into dichloromethane solution (100 mL), where a solid was precipitated out, filtered, the filter cake was spun with methanol for three times, after spin-dried, (S)-1-bromo-3-(pyrrolidin-2-yl)imidazo[1,5-a]pyrazin-8-amine hydrobromide (1.16 g, yield: ~100%) was obtained. Light brown solid, LCMS(ESI):m/z 282 [M+1]$^+$.

Step 1g, preparation of tert-butyl (S)-2-(8-amino-1-bromoimidazo[1,5-a]pyrazin-3-yl)pyrrolidine-1-carboxylate (compound 110): At 0° C., triethylamine (0.81 g, 8.0 mmol, 2.5 equivalents) was added into a solution of (S)-1-bromo-3-(pyrrolidin-2-yl)imidazo[1,5-a]pyrazin-8-amine hydrobromide (compound 109) (1.16 g, 3.2 mmol, 1.0 equivalent) in dichloromethane (30 mL), then a solution of BOC anhydride (0.72 g, 3.3 mmol, 1.05 equivalents) in dichloromethane (5 mL) was slowly added drop-wise, and the reaction solution was reacted for 25 minutes at 0° C. The reaction solution was diluted with dichloromethane (150 mL) and washed with salt water (100 mL×2), the organic phase was dried over anhydrous sodium sulfate and filtered, the filtrate was spin-dried, the remainder was purified by column chromatography (eluent:dichloromethane:methanol=80:1) to obtain tert-butyl (S)-2-(8-amino-1-bromoimidazo[1,5-a]pyrazin-3-yl)pyrrolidine-1-carboxylate (1.08 g, yield: 88.5%). White foamy substance; LCMS(ESI):m/z 382 [M+1]$^+$.

Step 1h, preparation of tert-butyl S)-2-(8-amino-1-(4-(benzyloxy)phenyl)imidazo[1,5-a]pyrazin-3-yl)pyrrolidine-1 -carboxylate (compound 301-1): 4-benzyloxybenzeneboronic acid (0.77 g, 3.4 mmol, 1.5 equivalents), a solution of potassium carbonate (0.95 g, 6.9 mmol, 3.0 equivalents) in water (12 mL), and [1,1'-bis(diphenylphosphino)ferrocene] dichloropalladium(II) (0.17 g, 0.23 mmol, 0.1 equivalent) were added into a solution of tert-butyl (S)-2-(8-amino-1-bromoimidazo[1,5-a]pyrazin-3-yl)pyrrolidine-1-carboxylate (compound 110) (0.86 g, 2.3 mmol, 1.0 equivalent) in 1,4-dioxane (36 mL). Under the protection of nitrogen, the reaction solution was heated to 100° C. and refluxed overnight. The reaction solution was spin-dried, the remainder was purified by column chromatography (eluent:dichloromethane:methanol=60:1) to obtain tert-butyl (S)-2-(8-amino-1-(4-(benzyloxy)phenyl)imidazo[1,5-a]pyrazin-3-yl) pyrrolidine-1-carboxylate (0.95 g, yield: 85.0%). Light brown foamy substance; LCMS(ESI):m/z 486 [M+1]$^+$.

Step 1i, preparation of (S)-1-(4-(benzyloxy)phenyl)-3-(pyrrolidin-2-yl)imidazo[1,5-a]pyrazin-8-amine (compound 302-1): Trifluoroacetic acid (4.0 mL) was added into a solution of tert-butyl (S)-2-(8-amino-1-(4-(benzyloxy)phenyl)imidazo[1,5-a]pyrazin-3-yl)pyrrolidine-1-carboxylate (compound 301-1) (0.95 g, 1.96 mmol, 1.0 equivalent) in dichloromethane (20 mL) and stirred for 1 hour at room temperature. The reaction solution was poured into saturated sodium carbonate solution (100 mL) and extracted with dichloromethane(100 mL×4), the organic phase was dried over anhydrous sodium sulfate and filtered, the filtrate was spin-dried and purified by column chromatography (eluent: dichloromethane:methanol:triethylamine=15:1:0.05) to obtain (S)-1-(4-(benzyloxy)phenyl)-3-(pyrrolidin-2-yl)imidazo[1,5-a]pyrazin-8-amine (0.57 g, yield: 75.4%). Pale yellow solid; LCMS(ESI); m/z 386 [M+1]$^+$.

Step 1j, preparation of (S)-1-(2-(8-amino-1-(4-(benzyloxy)phenyl)imidazo[1,5-a]pyrazin-3-yl)pyrrolidin-1-yl) but-2-yn -1-one (compound 1): At 0° C., triethylamine (0.22 g, 2.22 mmol, 1.5 equivalents) and 2-(7-azobenzotriazol-1-yl)-N,N,N',N'-tetramethyluronium hexafluorophosphate (0.62 g, 1.63 mmol, 1.1 equivalents) were added into a solution of 2-butynoic acid (0.14 g, 1.63 mmol, 1.1 equivalents) in dichloromethane (17 mL), then a solution of (S)-1-(4-(benzyloxy)phenyl)-3-(pyrrolidin-2-yl)imidazo[1,5-a]pyrazin-8-amine (compound 302-1) (0.57 g, 1.48 mmol, 1.0 equivalent) in dichloromethane (20 mL) was slowly added dropwise with, and the reaction solution was reacted for 25 minutes at 0° C. The reaction solution was diluted with dichloromethane and purified by column chromatography (eluent:dichloromethane:tnethanol=60:1) to obtain (S)-1-(2-(8-amino-1-(4-(benzyloxy)phenyl)imidazo[1,5-a]pyrazin-3-yl)pyrrolidin-1-yl)but-2-yn -1-one (545 mg, yield: 81.3%). Light yellow solid; LCMS(ESI):m/z 452 [M+1]$^+$. $^1$HNMR (CDCl$_3$, 500 MHz): δ7.75-7.76 (m, 1H), 7.53-7.57 (m, 2H), 7.28-7.46 (m, 5H), 7.05-7.10 (m, 3H), 5.42-5.45 (m, 1H), 5.12 (s, 5.09-5.25, (m, 2H), 3.82-3.91 (m, 2H), 2.30-2.55 (m, 3H), 2.01-2.04 (m, 1H), 1.97 (s, 3H).

Example 2: Preparation of (S)-1-(2-(8-amino-1-(4-((4-(trifluoromethyl)benzyl)oxy)phenyl)imidazo[1,5-a]pyrazin-3-yl)pyrrolidin-1-yl)but-2-yn-1-one (compound 2)

Step 2a, preparation of 1-bromo-4-((4-(trifluoromethyl)benzyl)oxy)benzene (compound 204-2): p-(trifluoromethyl)benzyl bromide (compound 201-2) (1.20 g, 5 mmol, 1.0 equivalent), p-bromophenol (compound 203-2) (0.95 g, 5.5 mmol, 1.1 equivalents), potassium carbonate (1.38 g, 10 mmol, 2.0 equivalents) and acetonitrile (50 mL) were added into an eggplant shaped. flask, heated and refluxed for 3 hours. The reaction solution was concentrated, the residue was purified by column chromatography (eluent:petroleum ether:ethyl acetate=20:1) to obtain 1-bromo-4-((4-(trifluoromethyl)benzyl)oxy)benzene (1.60 g, yield: 97.0%). Colorless solid.

Step 2b, preparation of 4,4,5,5-tetramethyl-2-(4-((4-(trifluoromethyl)benzyl)oxy)phenyl)-1,3,2-dioxaborolane (compound 206-2): bis(pinacolato)diboron (compound 205) (1.35 g, 5.30 mmol, 1.1 equivalent), potassium acetate (0.98 g, 9.60 mmol, 2.0 equivalents), and [1,1'-Bis(diphenylphosphino)ferrocene]dichloropalladium(II) (0.37 g, 0.50 mmol, 0.1 equivalent) were added into a solution of 1-bromo-4-((4-(trifluoromethyl)benzyl)oxy)benzene (compound 204-2) (1.60 g, 4.80 mmol, 1.0 equivalent) in 1,4-dioxane (500 mL), the reaction solution was heated to 100° C. and refluxed overnight under protection of nitrogen. The reaction solution was spin-dried, the remainder was purified by column chromatography (eluent:petroleum ether:ethyl acetate=20:1) to obtain 4,4,5,5-tetramethyl-2-(4-((4-(trifluoromethyl)benzyl)oxy)phenyl)-1,3,2-dioxaborolane (1.32 g, yield: 73%). Colorless solid.

Step 2c, preparation of tert-butyl (S)-2-(8-amino-1-(4-((4-(trifluoromethyl)benzyl)oxy)phenyl)imidazo[1,5-a]pyrazin-3-yl)pyrrolidine-1-carboxylate (compound 301-2): 4,4,5,5-tetramethyl-2-(4-((4-(trifluoromethyl)benzyl)oxy)phenyl)-1,3,2-dioxaborolane (compound 206-2) (0.119 g, 0.31 mmol, 1.5 equivalents), a solution of potassium carbonate (0.087 g, 0.63 mmol, 3.0 equivalents) in water (3 mL), and [1,1'-bis(diphenylphosphino)ferrocene]dichloropalladium (II) (0.015 g, 0.02 mmol, 0.1 equivalent) were added into a solution of tert-butyl (S)-2-(8-amino-1-bromoimidazo[1,5-a]pyrazin-3-yl)-pyrrolidine-1-carboxylate (compound 110) (0.08 g, 0.21 mmol, 1.0 equivalent) in 1,4-dioxane (12 mL). The reaction solution was heated to 100° C. and refluxed overnight under the protection of nitrogen. The reaction solution was spin-dried, the remainder was purified by column chromatography (eluent:dichloromethane:methanol=40:1) to obtain tert-butyl(S)-2-(8-amino-1-(4-((4-(trifluoromethyl)benzyl)oxy)phenyl)imidazo[1,5-a]pyrazin-3-yl)pyrrolidine-1-carboxylate (0.100 g, yield: 86.0%). Light brown foamy substance; LCMS(ESI):m/z 554 [M+1]$^+$.

Step 2d, preparation of (S)-3-(pyrrolidin-2-yl)-1-(4-((4-(trifluoromethyl)benzyl)oxy)phenyl)imidazo[1,5-a]pyrazin-8-amine) (compound 302-2): Trifluoroacetic acid (2.0 mL) was added into a solution of tert-butyl (S)-2-(8-amino-1-(4-((4-(trifluoromethyl)benzyl)oxy)phenyl)imidazo[1,5-a]pyrazin-3-yl)pyrrolidine-1-carboxylate (compound 301-2) (0.10 g, 0.18 mmol, 1.0 equivalent) in dichloromethane (10 mL), and stirred for 1 hour at room temperature. The reaction solution was poured into saturated sodium carbonate solution (100 mL) and extracted with dichloromethane (100 mL×4), the organic phase was dried over anhydrous sodium sulfate, filtered, the filtrate was spin-dried and purified by column chromatography (eluent:dichloromethane:methanol:triethylamine=15:1:0.05) to obtain (S)-3-(pyrrolidin-2-yl)-1-(4-((4-(trifluoromethyl)benzyl)oxy)phenyl)imidazo[1,5-a]pyrazin-8-amine (0.065 g, yield: 80.0%) Light yellow solid; LCMS(ESI):m/z 454 [M+1]$^+$.

Step 2e, preparation of (S)-1-(2-(8-amino-1-(4-((4-(trifluoromethyl)benzyl)oxy)phenyl)imidazo[1,5-a]pyrazin-3-yl)pyrrolidin-1-yl)but-2-yn-1-one (compound 2): At 0° C., triethylamine (0.021 g, 0.21 mmol, 1.5 equivalents) and 2-(7-azobenzotriazolyl)-N,N,N',N'-tetramethyluronium hexafluorophosphate (0.059 g, 0.154 mmol, 1.1 equivalents) were added into a solution of 2-butynoic acid (0.013 g, 0.154 mmol, 1.1 equivalents) in dichloromethane (10 mL), and then a solution of (S)-3-(pyrrolidin-2-yl)-1-(4-((4-(trifluoromethyl)benzyl)oxy)phenyl)imidazo[1,5-a]pyrazin-8-amine) (compound 302-2) (0.065 g, 0.14 mmol, 1.0 equivalent) in dichloromethane (5 mL) was slowly added dropwise, and the reaction solution was reacted for 25 minutes at 0° C. The reaction solution was diluted with dichloromethane and purified by column chromatography (eluent:dichloromethane:methanol=20:1) to obtain (S)-1-(2-(8-amino-1-(4-((4-(trifluoromethyl)benzyl)oxy)phenyl)imidazo[1,5-a]pyrazin-3-yl)pyrrolidin-1-yl)but-2-yn-1-one (50 mg, yield: 69.0%). Colorless solid; LCMS(ESI): m/z 520 [M+1]$^+$. $^1$HNMR(CDCl$_3$, 500 MHZ): δ7.78-7.77 (d, 1H), 7.67-7.65 (d, 2H), 7.58-7.54 (t, 4H), 7.09-7.00 (m, 3H), 5.42-5.39 (m, 1H), 5.19 (s, 2H), 5.09-5.25 (m, 2H), 3.91-3.82 (m, 2H), 2.55-2.31 (m, 3H), 2.07-2.01 (m, 1H), 2.00 (s,3H).

Example 3: Preparation of (S)-1-(2-(8-amino-1-(4-((4-fluorobenzyl)oxy)phenyl)imidazo[1,5-a]pyrazin-3-yl)pyrrolidin-1-yl) but-2-yn-1-one) (compound 3)

Step 3a, preparation of 1-bromo-4-((4-fluorobenzyl)oxy) benzene (compound 204-3): A solution of 4-bromophenol (compound 203-2) (0.60 g, 3.47 mmol, 1.3 equivalents) in acetonitrile (12 mL ,) was added into a reaction vessel, then potassium carbonate (0.74 g, 5.34 mmol, 2.0 equivalents) and 4-fluorobenzyl bromide (compound 201-3) (0.50 g, 2.67 mmol, 1.0 equivalent) were added, and the reaction solution was heated to 80° C. and refluxed for 3.5 hours under the protection of nitrogen. The reaction solution was spin-dried, the remainder was dissolved in ethyl acetate (100 mL) and washed with water (100 mL), the organic phase was mixed with silica gel and spin-dried, the remainder was purified by column chromatography (eluent:petroleum ether) to obtain 1-bromo-4-((4-fluorobenzyl)oxy)benzene (0.92 g, yield: ~100%). White solid.

Step 3b, preparation of 2-(4-((4-fluorobenzyl)oxy)phenyl)-4,4,5,5-tetramethyl-1,3,2-dioxaborolane (compound 206-3): Bis(pinacolato)diboron (205) (1.00 g, 3.93 mmol, 1.2 equivalents), potassium acetate (0.80 g, 8.18 mmol, 2.5 equivalents), and [1,1'-bis(diphenylphosphino)ferrocene]dichloropalladium(II) (0.24 g, 0.33 mmol, 0.1 equivalent) were added into a solution of 1-bromo-4-((4-fluorobenzyl)oxy)benzene (compound 204-3) (0.92 g, 3.27 mmol, 1.0 equivalent) in 1,4-dioxane (30 mL). The reaction solution was heated to 100° C. and refluxed overnight under the protection of nitrogen. The reaction solution was spin-dried, the remainder was purified by column chromatography (eluent:petroleum ether:ethyl acetate=50:1) to obtain 2-(4-((4-fluorobenzyl)oxy)phenyl)-4,4,5,5-tetramethyl-1,3,2-dioxaborolane (0.95 g, yield: 88.8%) Yale yellow oily substance.

Step 3c: preparation of tert-butyl (S)-2-(8-amino-1-(4-((4-fluorobenzyl)oxy)phenyl)imidazo[1,5-a]pyrazin-3-yl)pyrrolidine-1-carboxylate (compound 301-3): 2-(4-((4-fluorobenzyl)oxy)phenyl)-4,4,5,5-tetramethyl-1,3,2-dioxaborolane (compound 206-3) (0.18 g, 0.55 mmol, 1.4 equivalents), a solution of potassium carbonate (0.16 g, 1.17 mmol, 3.0 equivalents) in water (3 mL), and [1,1'-bis(diphenylphosphino)ferrocene]dichloropalladium(II) (0.03 g, 0.04 mmol, 0.1 equivalent) were added into a solution of tert-butyl (S)-2-(8-amino-1-bromoimidazo[1,5-a]pyrazin-3-yl)pyrrolidine-1-carboxylate (compound 110) (0.15 g, 0.39 mmol, 1.0 equivalent) in 1,4-dioxane (9 mL). The reaction solution was heated to 100° C. and refluxed for 5 hours under the protection of nitrogen The reaction solution was spin-dried, the remainder was purified by column chromatography (eluent:dichloromethane:methanol=80:1) to obtain (S)-2-(8-amino-1-(4-((4-fluorobenzyl)oxy)phenyl)imidazo[1,5-a]pyrazin-3-yl)pyrrolidine-1-carb oxylate (0.21 g, yield: ~100%). Light brown solid; LCMS(ESI):m/z 504 [M+1]$^+$.

Step 3d, preparation of (S)-1-(4-((4-fluorobenzyl)oxy)phenyl)-3-(pyrrolidin-2-yl)imidazo[1,5-a]pyrazin-8-amine (compound 302-3): Trifluoroacetic acid (2.0 mL) was added into a solution of tert-butyl (S)-2-(8-amino-1-(4-((4-fluorobenzyl)oxy)phenyl)imidazo[1,5-a]pyrazin-3-yl)pyrrolidine-1-carboxylate (compound 301-3) (0.21 g, 0.42 mmol, 1.0 equivalent) in dichloromethane (10mL), and stirred for 50 minutes at room temperature. The reaction solution was poured into saturated sodium carbonate solution (100 mL) and extracted with dichloromethane (100 mL×3), the organic phase was dried over anhydrous sodium sulfate, filtered, the filtrate was spin-dried and purified by thin-layer chromatography (eluent:dichloromethane:methanol=5:1) to obtain (S)-1-(4-((4-fluorobenzyl)oxy)phenyl)-3-(pyrrolidin-2-yl)imidazo[1,5-a]pyrazin-8-amine (0.12 g, yield: 70.6%). Light brown solid; LCMS(ESI):m/z 404 [M+1]$^+$.

Step 3e, preparation of (S)-1-(2-(8-amino-1-(4-((4-fluorobenzyl)oxy)phenyl)imidazo[1,5-a]pyrazin-3-yl)pyrrolidin-1-yl) but-2-yn-1-one (compound 3): At 0° C., N,N-diisopropylethylamine (0.06 g, 0.45 mmol, 1.5 equivalents) and 2-(7-azobenzotriazolyl)-N,N,N',N',-tetramethyluronium hexafluorophosphate (0.13 g, 0.33 mmol, 1.1 equivalents) were added into a solution of 2-butynoic acid (0.03 g, 0.33 mmol, 1.1 equivalents) in dichloromethane (5 mL), then a solution of (S)-1-(4-((4-fluorobenzyl)oxy)phenyl)-3-pyrrolidin-2-yl)imidazo[1,5-a]pyrazin-8-amine (compound 302-3) (0.12 g, 0.30 mmol, 1.0 equivalent) dichloromethane (10 mL) was slowly added dropwise, and the reaction solution was reacted for 15 minutes at 0° C. The reaction solution was diluted with dichloromethaneand purified by column chromatography (eluent:dichloromethane:methanol=30:1) to obtain a crude product (95 mg), after a further purification by thin-layer chromatography (eluent:dichloromethane:methanol=10:1), (S)-1-(2-(8-amino-1-(4-((4-fluorobenzyl)oxy)phenyl)imidazo[1,5-a]pyrazin-3-yl)pyrrolidin-1-yl)but-2-yn-1-one (75 mg, yield: 53.6%) was obtained. Pale yellow solid; LCMS(ESI): m/z 470 [M+1]$^{30}$ , $^1$HNMR(CDCl$_3$, 500 MHz); δ7.75-7.77 (m, 1H), 7.54-7.58 (m, 2H), 7.41-7.44 (m, 2H), 7.03-7.11 (m, 5H), 5.41-5.44 (m, 1H), 5.08 (s, 2H), 3.78-3.94 (m, 2H), 2.50-2.55 (m, 1H), 2.29-2.35 (m, 1H), 1.98-2.07 (m, 2H), 1.93 (s, 3H).

Example 4: Preparation of (S)-1-(2-(8-amino-1-(4-(pyridin-2-ylmethoxy)phenyl)imidazo[1,5-a]pyrazin-3-yl)pyrrolidin-1-yl)but-2-yn-1-one (compound 5)

Step 4a, preparation of 2-((4-bromophenoxy)methyl)pyridine (compound 204-5): At 0° C., to a solution of 4-bromophenol (compound 203-2) (1.00 g, 5.78 mmol, 1.0 equivalent) in tetrahydrofuran (30 mL) was added 2-pyridinemethanol (compound 202-5) (0.63 g, 5.78 mmol, 1.0 equivalent) and triphenylphosphine (1.67 g, 6.36 mmol, 1.1 equivalents), under nitrogen atmosphere, further added diisopropyl azodiformate (MAD, 1.29 g, 6.36 mmol, 1.1 equivalents) dropwise, and the reaction solution was reacted for 2 hours at room temperature. The reaction solution was spin-dried, the remainder was purified by column chromatography (eluent:petroleum ether:ethyl acetate=10:1) to obtain 2-((4-bromophenoxy)methyl)pyridine (compound 204-5) (1.87 g, 7.08 mmol, 1.0 equivalent). Colorless solid; LCMS(ESI):m/z 264 [M+1]$^+$.

Step 4b, preparation of 2-((4-(4,4,5,5-tetramethyl-1,3,2-dioxaborolan-2-yl)phenoxy)methyl)pyridine (compound 206-5): Bis(pinacolato)diboron (compound 205) (2.16 g, 8.50 mmol, 1.2 equivalents), potassium acetate (1.74 g, 17.70 mmol, 2.5 equivalents), and [1,1'-bis(diphenviphosphino)ferrocene]dichloropalladium(II) (0.52 g, 0.71 mmol, 0.1 equivalent) were added into a solution of 2-((4-bromophenoxy)methyl)pyridine (compound 204-5) (1.87 g, 7.08 mmol, 1.0 equivalent) in 1,4-dioxane (60 mL), the reaction solution was heated to 100° C. and refluxed overnight under the protection of nitrogen. The reaction solution was spin-dried, the remainder was purified by column chromatography (eluent:petroleum ether:ethyl acetate=10:1) to obtain 2-((4-(4,4,5,5-tetramethyl-1,3,2-dioxaborolan-2-yl)phenoxy)methyl)pyridine (1.88 g, yield: 85.5%). Pale yellow oily substance.

Step 4c, preparation of tert-butyl (S)-2-(8-amino-1-(4-(pyridin-2-ylmethoxy)phenyl)imidazo[1,5-a]pyrazin-3-yl)pyrrolidine-1-carboxylate) (compound 301-5): 2-((4-(4,4,5,5-tetramethyl-1,3,2-dioxaborolan-2-yl)phenoxy)methyl)pyridine (compound 206-5) (0.28 g, 0.92 mmol, 1.4 equivalents), a solution of potassium carbonate (0.27 g, 1.95 mmol, 3.0 equivalents) in water (3 mL), and [1,1'-bis(diphenylphosphino)ferrocene]dichloropalladium(II) (0.05 g, 0.07 mmol, 0.1 equivalent) were added into a solution of tert-butyl (S)-2-(8-amino-1-bromoimidazo[1,5-a]pyrazin-3-yl)pyrrolidine-1-carboxylate (compound 110) (0.25 g, 0.65 mmol, 1.0 equivalent) in 1,4-dioxane (9 mL), and the reaction solution was heated to 100° C. and refluxed overnight under the protection of nitrogen. The reaction solution was spin-dried, the remainder was purified by column chromatography (eluent:dichloromethane:methanol=30:1) to obtain tert-butyl(S)-2-(8-amino-1-(4-(pyridin-2-ylmethoxy)phenyl)imidazo[1,5-a]pyrazin-3-yl)pyrrolidine-1-carboxylate) (0.28 g, yield: 87.5%). Light brown foamy substance, LCMS(ESI): m/z 487 [M+1]$^+$.

Step 4d, preparation of (S)-1-(4-(pyridin-2-ylmethoxy)phenyl)-3-(pyrrolidin-2-yl)imidazo[1,5-a]pyrazin-8-amine (compound 302-5): Trifluoroacetic acid (3.0 mL) was added into a solution of tert-butyl (S)-2-(8-amino-1-(4-(pyridin-2-ylmethoxy)phenyl)imidazo[1,5-a]pyrazin-3-yl)pyrrolidine-1-carboxylate) (compound 301-5) (0.28 g, 0.58 mmol, 1.0 equivalent) in dichloromethane (10 mL) and stirred for 1 hour at room temperature. The reaction solution was poured into saturated sodium carbonate solution (100 mL) and extracted with dichloromethane (100 mL×3, the organic phase was dried over anhydrous sodium sulfate, filtered, the filtrate was spin-dried and purified by column chromatography (eluent:dichloromethane:methanol:triethylamine=15: 1:0.1) to obtain (S)-1-(4-(pyridin-2-ylmethoxy)phenyl)-3-(pyrrolidin-2-yl)imidazo[1,5-a]pyrazin-8-amine (0.21 g, yield: 95.1%). Light brown foamy substance; LCMS(ESI): m/z 387 [M+1]$^+$.

Step 4e, preparation of (S)-1-(2-(8-amino-1-(4-(pyridin-2-ylmethoxy)phenyl)imidazo[1,5-a]pyrazin-3-yl)pyrrolidin-1 -yl)but-2-yn-1-one (compound 5): At 0° C., to a solution of 2-butynoic acid (0.05 g, 0.60 mmol, 1.1 equivalents) in dichloromethane (6 mL) was added N,N-diisopropylethylamine (0.10 g, 0.81 mmol, 1.5 equivalents) and 2-(7-azobenzotriazolyl)-N,N,N',N'-tetramethyluronium hexafluorophosphate (0.23 g, 0.60 mmol, 1.1 equivalents), then slowly added a solution of (S)-1-(4-(pyridin-2-ylmethoxy)phenyl)-3-(pyrrolidin-2-yl)imidazo[1,5-a]pyrazin-8-amine (compound 302-5) (0.21 g, 0.54 mmol, 1.0 equivalent) in dichloromethane (10 mL) dropwise, and the reaction solution was reacted for 15 minutes at 0° C. The reaction solution was diluted with dichloromethane and purified by column chromatography (eluent:dichloromethane:methanol=30:1) to obtain (S)-1-(2-(8-amino-1-(4-(pyridin-2-ylmethoxy)phenyl)imidazo[1,5-a]pyrazin-3-yl pyrrolidin-1-yl)but-2-yn-1 -one (223 mg, yield: 92.6%). Light brown foamy substance; LCMS(ESI): m/z 453 [M+1]$^+$, $^1$HNMR (CDCl$_3$, 500 MHz): δ8.61-8.62 (m, 1H), 7.71-7.75 (m, 2H), 7.52-7.57 (m, 3H), 7.23-7.30 (m, 1H), 7.04-7.12 (m, 3H), 5.42-5.45 (m, 1H), 5.27 (s, 2H), 3.68-3.89 (m, 2H), 2.51-2.54 (m, 2H), 2.31-2.32 (m, 1H), 2.03-2.05 (m, 1H), 1.97 (s, 3H).

Example 5: Preparation of (S)-1-(2-(8-amino-1-(4-((4-fluoropyridin-2-yl)methoxy)phenyl)imidazo[1,5-a]pyrazin-3-yl)pyrrolidine-1one (compound 6)

Step 5a, preparation of 2-bromomethyl)-4-fluoropyridine (compound 201-6): 2-methyl-4-fluoropyridine (0.4 g, 3.60 mmol, 1.0 equivalent), NBS (0.64 g, 3.60 mmol, 1.0 equivalent), AIBN (59 mg, 0.36 mmol, 0.1 equivalent) and tetrachloromethane (8 mL) were added into a reaction vessel, heated to 80° C., and reacted overnight. The reaction solution was spin-dried and then purified by column chromatography (eluent:petroleum ether:ethyl acetate=20:1) to obtain 2-(bromomethyl)-4-fluoropyridine (0.152 g, yield: 22%). Yale yellow oily liquid; LCMS(ESI): m/z 190 [M+1]$^+$.

Step 5b, preparation of 2-((4-bromophenoxy)methyl)-4-fluoropyridine (compound 204-6): p-bromophenol (compound 203-2) (0.138 g, 0.8 mmol, 1.0 equivalent), 2-bromomethyl)-4-fluoropyridine (compound 201-6) (0.152 g, 0.8 mmol, 1.0 equivalent), potassium carbonate (0.166 g, 1.2 mmol, 1.2 equivalents) and acetonitrile (8 mL) were added into a reaction vessel, heated to 80° C., and reacted for 1.5 hours. The reaction solution was spin-dried and then purified by column chromatography (eluent:petroleum ether:ethyl acetate=10:1) to obtain 2-((4-bromophenoxy)methyl)-4-fluoropyridine (0.224 g, yield: 99%) Yale yellow solid; LCMS(ESI): m/z 282[M+1]$^+$.

Step 5c, preparation of 4-fluoro-2-((4-(4,4,5,5-tetramethyl-1,3,2-dioxaborolan-2-yl)phenoxy)methyl)pyridine (compound 206-6): 2-(4-bromophenoxymethyl)-4-fluoropyridine (compound 204-6) (0.224 g, 0.794 mmol, 1.0 equivalent) and bis(pinacolato)diboron (compound 205) (0.222 g, 0.874 mmol, 1.1 equivalent) were dissolved in dioxane (6 ml) and then potassium acetate (0.234 g, 2.38 mmol, 3.0 equivalents) and [1,1'-Bis(diphenylphosphino)ferrocene]dichloropalladium(II) (0.058 g, 0.079 mmol, 0.1 equivalent) were added, replaced with nitrogen for three times, and then reaction was carried out overnight at 100° C. After reaction, a crude product was obtained by concentration and purified by column chromatography (eluent:petroleum ether:ethyl acetate=10:1) to obtain 4-fluoro-2-((4-(4,4,5,5-tetramethyl-1,3,2-dioxaborolan-2-yl)phenoxy)methyl) pyridine (0.20 g, yield: 77%). Yale yellow solid; LCMS (ESI): m/z 330 [M+1]$^+$.

Step 5d, preparation of tert-butyl (S)-2-(8-amino-1-(4-((4-fluoropyridin-2-yl)methoxy)phenyl)imidazo[1,5-a] pyrazin-3-yl)pyrrolidine-1-carboxylate (compound 301-6): tert-butyl (S)-2-(8-amino-1-bromoimidazo[1,5-a]pyrazin-3-yl)pyrrolidine-1-carboxylate (compound 110) (0.095 g, 0.248 mmol, 1.0 equivalent) and 4-fluoro-2-((4-(4,4,5,5-tetramethyl-1,3,2-dioxaborolan-2-yl)phenoxy)methyl)pyridine (compound 206-6) (0.098 g, 0.298 mmol, 1.2 equivalents) were dissolved in dioxane (6 ml) and water (2 mL), and then potassium carbonate (0.103 g, 0.744 mmol, 3.0 equivalents) and [1,1'-Bis(diphenylphosphino)ferrocene]dichloropalladium(II) (18 mg, 0.025 mmol, 0.1 equivalent) were added. Replaced with nitrogen for three times and then reaction was carried out for 10 hours at 100° C. After reaction, a crude product was obtained by concentration and purified by column chromatography (eluent:petroleum ether:ethyl acetate=30:1) to obtain tert-butyl(S)-2-(8-amino-1-(4-((4-fluoropyridin-2-yl)methoxy)phenyl)imidazo[1,5-a] pyrazin-3-yl)pyrrolidine-1-carboxylate (0.12 g, yield: 96%). Yale yellow solid; LCMS(ESI): m/z 505 [M+1]$^+$.

Step 5e, preparation of (S)-1-(4-((4-fluoropyridin-2-yl) methoxy)phenyl)-3-(pyrrolidin-2-yl)imidazo[1,5-a]pyrazin-8-amine (compound 302-6): tert-butyl(S)-2-(8-amino-1-(4-((4-fluoropyridin-2-yl)methoxy)phenyl)imidazo[1,5-a] pyrazin-3-yl)pyrrolidine-1-carboxylate (compound 301-6) (0.12 g, 0.238 mmol, 1.0 equivalent) was dissolved in dichloromethane (5 mL), trifluoroacetic acid (1 mL) was further added therein, and then reaction was carried out for 0.5 hour at room temperature. The reaction mixture was diluted with dichloromethane (50 mL) and washed with saturated sodium carbonate solution (30 mL×2) and saturated table salt water (20 mL) successively, then the organic layer was mixed with silica gel, spin-dried, and then purified by column chromatography (eluent:dichloromethane:methanol:triethylamine=100:10:1) to obtain (S)-1-(4-((4-fluoropyridin-2-yl)methoxy)phenyl)-3-(pyrrolidin-2-yl)imidazo [1,5-a]pyrazin-8-amine (95 mg, yield: 99%). Yale yellow solid; LCMS(ESI): m/z 405 [M+1]$^+$.

Step 5f, preparation of (S)-1-(2-(8-amino-1-(4-((4-fluoropyridin-2-yl)methyoxy)phenyl)imidazo[1,5-a]pyrazin-3--yl)pyrrolidin-1-yl)but-2-yn-1-one (compound 6): (S)-1-(4-((4-fluoropyridin-2-yl)methoxy)phenyl)-3-(pyrrolidin-2-yl) imidazo[1,5-a]pyrazin-8-amine (compound 302-6) (95 mg, 0.235 mmol, 1.0 equivalent), 2-butynoic acid (22 mg, 0.258 mmol, 1.1 equivalents), HATU (98 mg, 0.258 mmol, 1.1 equivalents) and potassium carbonate (49 mg, 0.353 mmol, 1.5 equivalents) were added into N,N-dimethylformamide (3 mL) and reacted for 0.5 hour at 0° C. The reaction solution was diluted with water (20 mL) and extracted with dichloromethane (30 mL×3), the extract was dried over anhydrous sodium sulfate, concentrated, and purified by column chromatography (eluent:dichloromethane:methanol=20:1) to obtain (S)-1-(2-(8-amino-1-(4-((4-fluoropyridin-2-yl)methoxy)phenyl)imidazo[1,5-a]pyrazin-3-yl)pyrrolidin-1-yl)but-2-yn-1-one (18 mg, yield: 16%). Gray solid, melting point: 162.3-165.1° C. LCMS(ESI): m/z 471 [M+1]$^+$, $^1$HNMR(DMSO-d$_6$, 500 MHz): δ8.66-8.62 (m , 1H), 7.79-7.72 (m, 1H), 7.54-7.44 (m, 3H), 7.34-7.30 (m, 1H), 7.18 (d, J=9.0 Hz, 2H), 7.08-7.03 (m, 1H), 6.03-5.97 (m, 2H), 5.69-5.43 (m, 1H), 5.27 (s, 2H), 3.82-3.79 (m, 1H), 3.58-3.55 (m, 1H), 2.40-2.08 (m, 3H), 2.03-1.94 (m, 4H).

Example 6: Preparation of (S)-1-(2-(8-amino-1-(6-(benzyloxy)pyridin-3-yl)imidazo[1,5-a]pyrazin-3-yl)pyrrolidin-1 -yl)but-2-yn-1-one (compound 9)

Step 6a, preparation of 2-(benzyloxy)-5-bromopyridine (compound204-9): Benzyl alcohol (2.59 g, 24.0 mmol, 1.2 equivalents) was added into N,N-dimethylformamide (30 mL) solution of sodium hydride (1.04 g, 26.0 mmol, 1.3 equivalents) at 0° C., the mixture was stirred for 1 hour at 0° C., further added 2,5-dibromopyridine (4.74 g, 20 mmol, 1.0 equivalent), and the reaction solution was reacted overnight at room temperature. The reaction solution was diluted with ethyl acetate (300 mL) and washed with semi-saturated table salt solution (300 mL×4), the organic phase was dried over anhydrous sodium sulfate and filtered. The filtrate was spun with petroleum ether for three times, the remainder was purified by column chromatography (eluent:petroleum ether:ethyl acetate=200:1) to obtain 2-(benzyloxy)-5-bromopyridine (3.76 g, yield: 71.2%). Colorless oily substance; LCMS(ESI): m/z 264 [M+1]$^+$.

Step 6b, preparation of 2-benzyloxy-5-(4,4,5,5-tetramethyl-1,3,2-dioxaborolan-2-yl)pyridine (compound 206-9): Bis(pinacolato)diboron (compound 205) (4.34 g, 17.1 mmol, 1.2 equivalents), potassium acetate (3.48 g, 35.5 mmol, 2.5 equivalents), and [1,1'-bis(diphenylphosphino)ferrocene]dichloropalladium(II) (1.16 g, 1.4 mmol, 0.1 equivalent) were added into 1,4-dioxane solution (50 mL) of 2-(benzyloxy)-5-bromopyridine (compound 204-9) (3.67 g, 14.2 mmol, 1.0 equivalent), and the reaction solution was heated to 100° C. and refluxed overnight under the protection of nitrogen. The reaction solution was spin-dried, the remainder was purified by column chromatography (eluent: petroleum ether:dichloromethane=2:1) to obtain 2-(benzyloxy)-5-(4,4,5,5-tetramethyl-1,3,2-dioxaborolan-2-yl)pyridine (2.63 g, yield: 59.5%). White solid; LCMS(ESI): m/z 312 [M+1]$^+$.

Step 6c, preparation of tert-butyl (S)-2-(8-amino-1-(6-(benzyloxy)pyridin-3-yl)imidazo[1,5-a]pyrazin-3-yl)pyrrolidine-1-carboxyl ate (compound 301-9): 2-(benzyloxy)-5-(4,4,5,5-tetramethyl-1,3,2-dioxaborolan-2-yl)pyridine (compound 206-9) (0.41 g, 1.31 mmol, 2.0 equivalents), a solution of potassium carbonate (0.27 g, 1.95 mmol, 3.0 equivalents) in water (3 mL), and [1,1'-bis(diphenylphosphino)ferrocene]dichloropalladium(II) (0.05 g, 0.07 mmol, 0.1 equivalent) were added into a solution of tert-butyl (S)-2-(8-amino-1-bromoimidazo[1,5-a]pyrazin-3-yl)pyrrolidine-1-carboxylate (compound 110) (0.25 g, 0.65 mmol, 1.0 equivalent) in 1,4-dioxane (9 mL), the reaction solution was heated to 100° C. and refluxed for 4 hours under the protection of nitrogen. The reaction solution was spin-dried, the remainder was purified by column chromatography (eluent:dichloromethane:methanol=50:1) to obtain tert-butyl (S)-2-(8-amino-1-(6-(benzyloxy)pyridin-3-yl)imidazo [1,5-a]pyrazin-3-yl)pyrrolidine-1-carboxyl ate (0.25 g, yield: 79.1%). Light brown foamy substance; LCMS(ESI): m/z 487 [M+1]$^+$.

Step 6d, preparation of (S)-1-(6-(benzyloxy)pyridin-3-yl)-3-(pyrrolidin-2-yl)imidazo[1,5-a]pyrazin-8-amine (compound 302-9): Trifluoroacetic acid (3.0 mL) was added into a solution of tert-butyl (S)-2-(8-amino-1-(6-(benzyloxy) pyridin-3-yl)imidazo[1,5-a]pyrazin-3-yl)pyrrolidine-1-carboxyl ate (compound 301-9) (0.25 g, 0.51 mmol, 1.0 equivalent) in dichloromethane (10 mL) and stirred for 50 minutes at room temperature The reaction solution was poured into saturated sodium carbonate solution (100 mL) and extracted with dichloromethane (100 mL×3), the organic phase was dried over anhydrous sodium sulfate and filtered, the filtrate was spin-dried and purified by column chromatography (eluent:dichloromethane:methanol:triethylamine=15:1: 0.05) to obtain a crude product (0.15 g), the crude product was purified by chromatography (eluent:dichloromethane: methanol=5:1) to obtain (S)-1-(6-(benzyloxy)pyridin-3-yl)-3-(pyrrolidin-2-yl)imidazo[1,5-a]pyrazin-8-amine (0.14g, yield: 71.1%). White solid; LCMS(ESI): m/z 387 [M+1]$^+$.

Step 6e, preparation of (S)-1-(2-(8-amino-1-(6-(benzyloxy)pyridin-3-yl)imidazo[1,5-a]pyrazin-3-yl)pyrrolidin-1-yl)but-2-yn-1-one (compound 9): At 0° C., to a solution of 2-butynoic acid (0.034 g, 0.40 mmol, 1.1 equivalents) in dichloromethane (4 mL) was added N,N-diisopropylethylamine (0.07 g, 0.54 mmol, 1.5 equivalents) and 2-(7-azobenzotriazolyl)-N,N,N',N',-tetramethyluronium hexafluorophosphate (0.15 g, 0.40 mmol, 1.1 equivalents), and then slowly added a solution of (S)-1-(6-(benzyloxy)pyridin-3-yl)-3-(pyrrolidin-2-yl)imidazo[1,5-a]pyrazin-8-amine (compound 302-9) (0.14 g, 0.36 mmol, 1.0 equivalent) in dichloromethane (11 mL) dropwise, and the reaction solution was reacted for 15 minutes at 0° C. The reaction solution was diluted with dichloromethane and purified by column chromatography (eluent:dichloromethane:methanol=30:1) to obtain (S)-1-(2-(8-amino-1-(6-(benzyloxy)pyridin-3-yl)imidazo[1,5-a]pyrazin-3-yl)pyrrolidin-1-yl)but -2-yn-1-one (140 mg, yield: 85.9%). White solid; LCMS(ESI): m/z 453 [M+1]$^+$; $^1$HNMR(CDCl$_3$, 500 MHz): δ8.42-8.43 (m, 1H), 7.77-7.89 (m, 2H), 7.33-7.49 (m, 6.91-7.13 (m, 2H), 5.42-5.46 (m, 3H), 3.68-3.90 (m, 2H), 2.01-2.53 (m, 4H), 1.97 (s, 3H).

Example 7: Preparation of (S)-1-(2-(8-amino-1-(4-phenethoxyphenyl)imidazo[1,5-a]pyrazin-3-yl)pyrrolidin-1-yl)but-2-yn-1-one (compound 17)

Step 7a, preparation of 4,4,5,5-tetramethyl-2-(4-phenethoxyphenyl)-1,3,2-dioxaborolane (compound 206-17): 4-(4,4,5,5-tetramethyl-1,3,2-dioxaborolan-2-yl)phenol (1.1 g, 5.0 mmol, 1.0 equivalent), phenylethanol (compound 202-17) (0.6 g, 5.0 mmol, 1.0 equivalent), triphenylphosphine (3.93 g, 15.0 mmol, 3.0 equivalents) and diisopropyl azodicarboxylate (2.87 g, 16.5 mol, 3.5 equivalents) were added into a reaction vessel and reacted for 4 hours at room temperature. The reaction solution was diluted with dichloromethane (50 mL) and washed with semi-saturated table salt water solution (50mL×3), the organic phase was mixed with silica gel, spin-dried, and purified by column chromatography (eluent:dichloromethane:n-hexane=1:2) to obtain 4,4,5,5-tetramethyl-2-(4-phenethoxyphenyl)-1,3,2-dioxaborolane (0.9 g, yield: 56.2%). Pink solid; LCMS(ESI): m/z 326[M+1]$^+$.

Step 7b, preparation of (S)-tert-butyl 2-(8-amino-1-(4-phenethoxyphenyl)imidazo[1,5-a]pyrazin-3-yl)pyrrolidine-1-carboxylate (compound 301-17): (S)-tert-butyl -2-(8-amino-1-bromoimidazo[1,5-a]pyrazin-3-yl)pyrrolidine-1-carboxylate (compound 110) (0.58 g, 1.5 mmol, 1.0 equivalent), 4,4,5,5-tetramethyl-2-(4-phenethoxyphenyl)-1, 3,2-dioxaborolane (compound 206-17) (0.58 g, 1.8 mmol, 1.2 equivalents), tetrakis(triphenylphosphine)palladium (0.17 g, 0.15 mmol, 0.1 equivalent), sodium carbonate (0.32 g, 3 mol, 2.0 equivalents), 1,4-dioxane (10 mL) and water (3 mL) were added into a reaction vessel and reacted overnight in 80° C. oil bath. The reaction solution was diluted with dichloromethane (100 mL) and washed with saturated table salt solution (50 mL×3), the organic phase was spin-dried and purified by column chromatography (eluent:ethyl acetate:cyclohexane=2:1) to obtain (S)-tert-butyl 2-(8-amino-1-(4-phenethoxyphenyl)imidazo[1,5-a]pyrazin-3-yl) pyrrolidien-1-carboxylate (0.6 g, yield: 80.0%). Yale yellow solid; LCMS(ESI): m/z 500[M+1]$^+$.

Step 7c, preparation of (S)-1-(4-phenethoxyphenyl)-3-(pyrrolidin-2-yl)imidazo[1,5-a]pyrazin-8-amine (compound 302-17): (S)-tert-butyl 2-(8-amino-1-(4-phenethoxyphenyl) imidazo[1,5-a]pyrazin-3-yl)pyrrolidine-1-carboxylate (compound 301-17) (0.6 g, 1.2 mmol, 1.0 equivalent), trifluoroacetic acid (15 mL), and dichloromethane (20mL) were added into a reaction vessel and reacted for 1 hour at room temperature. The reaction solution was diluted with dichloromethane (100 mL), the pH value was regulated to be slightly alkaline with saturated sodium bicarbonate, the organic phase was spin-dried, after purification by column chromatography (eluent:dichloromethane:methanol=10:1), (S)-1-(4-phenethoxyphenyl)-3-(pyrrolidin-2-yl)imidazo[1, 5-a]pyrazin-8-amine (0.4 g, yield: 83.3%) was obtained. Yellow solid; LCMS(ESI): m/z 500[M+1]$^+$.

Step 7d, preparation of (S)-1-(2-(8-amino-1-phenethoxyphenyl)imidazo[1,5-a]pyrazin-3-yl)pyrrolidin-1-yl)but-2-yn -1-one (compound 17): (S)-1-(4-phenethoxyphenyl)-3-(pyrrolidin-2-yl)imidazo[1,5-a]pyrazin-8-amine (compound 302-17) (0.40 g, 1.0 mmol, 1.0 equivalent), propiolic acid (0.084 g, 1.0 mmol, 1.0 equivalent), HATU (0.46 g, 1.2 mol, 1.2 equivalents), DIEA (0.26 g, 2.0 mmol, 2.0 equivalents) and dichloromethane (10 mL) were added into a reaction vessel and reacted for 15 minutes in ice-water bath. The reaction solution was processed by column chromatography (eluent:dichloromethane:methanol=20:1) to obtain (S)-1-(2-(8-amino-1-(4-phenethoxyphenyl)imidazo[1,5-a]pyrazin-3-yl)pyrrolidin-1-yl)but-2-yn -1-one (200 mg, yield: 43%). Almost white solid, melting point: 91-93° C. LCMS(ESI): m/z 466[M+1]$^+$, $^1$HNMR(DMSO-d6, 600 MHz): δ7.76 (d, J=5 Hz, 1H), δ7.71 (d, J=5 Hz, 1H), δ7.46 (m, 5H), 7.33 (m, 10H), 7.22 (t, J=7 Hz, 2H), 7.05 (m, 6H), 7.02 (d, J=5 Hz, 1H), 5.90 (m, 5H), 5.65 (s, 1H), 5.42 (s, 1H), 4.25 (m, 5H), 3.77 (m, 3H), 3.06 (m, 5H), 2.00 (s, 5H), 1.62 (s, 3H).

Example 8: Preparation of (S)-1-(2-(8-amino-1-(4-(benzyloxy)phenyl)imidazo[1,5-a]pyrazin-3-yl)pyrrolidin-1-yl)prop-2-en -1-one (compound 21)

(S)-1-(4-(benzyloxy)phenyl)-3-(pyrrolidin-2-yl)imidazo [1,5-a]pyrazin-8-amine (compound 302-1) (161 mg, 0.418 mmol, 1.0 equivalent) was dissolved in tetrahydrofuran (10 mL) and cooled to 0° C. by ice-water bath. Acryloyl chloride (35 mg, 0.418 mmol, 1.0 equivalent) dissolved in tetrahydrofuran (5 mL) was added drop by drop, then reaction was carried out for 10 minutes at 0° C. After the reaction was completed, the reaction mixture was concentrated to give a crude product, which was processed by thin layer chromatography (dichloromethane:methanol=30:1) to obtain (S)-1-(2-(8-amino-1-(4-(benzyloxy)phenyl)imidazo[1,5-a] pyrazin-3-yl)pyrrolidin-1-yl)prop-2-en -1-one (35 mg, yield: 19%). White solid, melting point: 100.2-103.1° C. LCMS(ESI): m/z 440[M+1]$^+$, $^1$HNMR(CDCl$_3$, 500 MHz): δ7.79 (d, J=6.5 Hz, 1H), 7.55-7.52 (m, 2H), 7.46-7.26 (m, 5H), 7.08-7.06 (m, 3H), 6.49-6.43 (m, 1H), 6.35-6.31 (m, 1H), 5.69-5.66 (m, 1H), 5.49-5.33 (m, 2H), 5.12 (s, 2H), 3.92-3.87 (m, 1H), 3.76-3.70 (m, 1H), 2.69-2.61 (m, 1H), 2.50-2.43 (m, 1H), 2.35-1.98(m, 3H).

Example 9: Preparation of (S)-1-(2-(8-amino-1-(6-(benzyloxy)pyridin-3-yl)imidazo[1,5-a]pyrazin-3-yl) pyrrolidin-1-yl)prop -2-en-1-one (compound 25)

At 0° C., to a solution of crylic acid (0.04 g, 0.59 mmol, 1.1 equivalents) in N,N-dimethylformamide (5 mL) was added 4-dimethylaminopyridine (0.18 g, 1.47 mmol, 3.0 equivalents) and 1-ethyl-(3-dimethyllaminopropyl)carbodiie hydrochlide (0.14 g, 0.74 mmol, 1.5 equivalents), then further slowly added a solution of (S)-1-(6-(benzyloxy) pyridin-3-yl)-3-(pyrrolidin-2-yl)imidazo[1,5-a]pyrazin-8-amine (compound 302-9) (0.19 g, 0.49 equivalent) in N,N-dimethylformamide (7 mL) dropwise, the reaction solution was reacted for 15 minutes at 0° C., further added the N,N-dimethylformamide solution (8 mL), and the reaction solution was reacted for 7 hours at room temperature. The reaction solution was diluted with ethyl acetate (200 mL) and washed with semi-saturated table salt water solution (200 mL×3), the organic phase was washed with 2% acetic acid solution (100 mL×1), saturated sodium bicarbonate solution (100 mL×1) and saturated table salt water solution (100 mL×1) successively, the aqueous phase was regulated to pH≈7 and extracted with ethyl acetate (100 mL×1), the resultant organic phase was washed with saturated sodium bicarbonate solution (100 mL×1), the organic phases were combined together, spin-dried, recrystallized with methanol, and further purified by column chromatography (eluent:dichloromethane:methanol=20:1) to obtain a crude product (30 g), which was further purified by thin layer chromatography (dichloromethane:methanol=10:1) to get (S)-1-(2-(8-amino-1-(6-(benzyloxy)pyridin-3-yl)imidazo[1,5-a]pyrazin-3-yl)pyrrolidin-1-yl)prop -2-en-1-one (23 mg, yield: 10.7%). White solid; LCMS(ESI): m/z 441 [M+1]$^+$, $^1$HNMR(CDCl$_3$, 500 MHz): δ8.42-8.43 (m, 1H), 7.81-7.88 (m, 2H), 7.33-7.49 (m, 5H), 7.11-7.12 (m, 1H), 6.91-6.93 (m, 1H), 6.31-6.50 (m, 2H), 5.67-5.70 (dd, 1H), 5.47-5.50 (m, 1H), 5.10-5.43 (m, 4H), 3.88-3.92 (m, 1H), 3.73-3.75 (m, 1H), 2.42-2.45 (m, 1H), 2.29-2.34 (m, 1H), 1.99-2.14 (m, 2H).

Example 10: Preparation of (S)-1-(2-(8-amino-1-(4-(pyridin-2-ylmethoxy)phenyl)imidazo[1,5-a]pyrazin-3-yl)pyrrolidin-1-yl)prop-2-en-1-one (compound 29)

At 0° C. to a solution of crylic acid (0.03 g, 0.48 mmol, 1.1 equivalents) in dichloromethane (10 mL) was added N,N-diisopropylethylamine (0.11 g, 0.66 mmol, 1.5 equivalents) and 2-(7-azobenzotriazoly)-N,N,N',N'-tetramethyluronium hexafluorophosphate (0.18 g, 0.48 mmol, 1.1 equivalents), further slowly added dropwise a solution of (S)-1-(4-(pyridin-2-ylmethoxy)phenyl)-3-(pyrrolidin-2-yl) imidazo[1,5-a]pyrazin-8-amine (compound 302-5) (0.17 g, 0.44 mmol, 1.0 equivalent) in mixed dichloromethane (20 mL) and tetrahydrofuran (10 mL), and the reaction solution was reacted for 15 minutes at 0° C. The reaction solution was diluted with dichloromethane and purified by column chromatography (eluent:dichloromethane:methanol=20:1) to get a crude product (90 mg), which was further purified by thin layer chromatography (dichloromethane:methanol=8:1) to obtain (S)-1-(2-(8-amino-1-(4-(pyridin-2-ylmethoxy)phenyl)imidazo[1,5-a]pyrazin-3-yl)pyrrolidin-1-yl) prop-2-en-1-one (60 mg, yield: 30.9% ). Light yellow solid; LCMS(ESI): m/z 441 [M+1]$^+$, $^1$HNMR(CDCl$_3$, 500 MHz): δ8.61-8.62 (m, 1H), 7.71-7.79 (m, 2H), 7.47-7.55 (m, 3H), 7.23-7.25 (m, 1H), 7.05-7.11 (m, 3H), 6.31-6.50 (m, 2H), 5.66-5.69 (dd, 1H), 5.46-5.49 (m, 1H), 5.30 (s, 4H), 3.88-3.91 (m, 1H), 3.70-3.76(m, 1H), 2.61-2.66 (m, 1H), 2.44-2.48 (m, 1H), 2.05-2.14 (m, 2H).
According to the preparation methods of Examples 1-10, the following compounds were further synthesized:
Compound 4
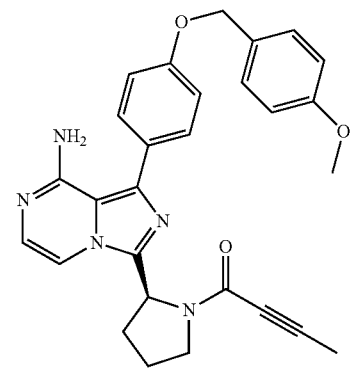
Compound 7
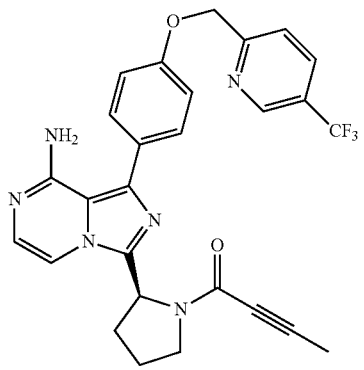
Compound 8
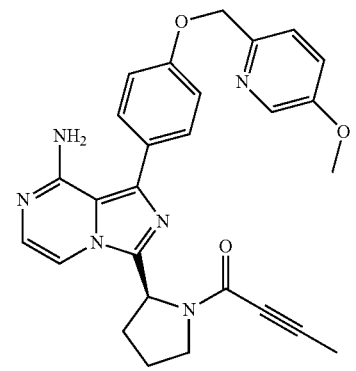
Compound 10
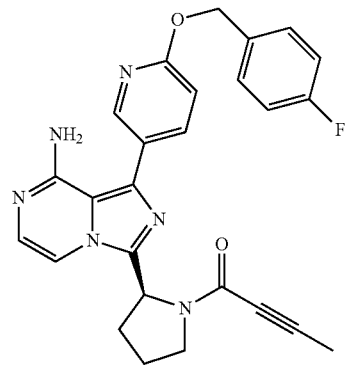
-continued
Compound 11
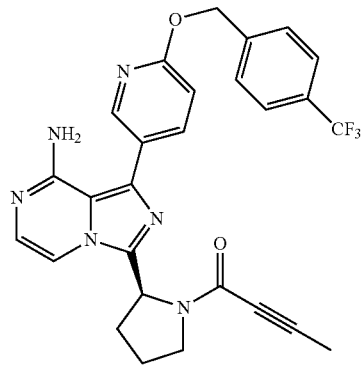
Compound 12
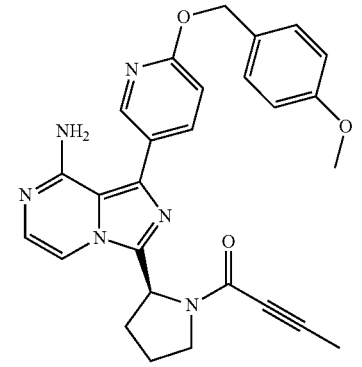
Compound 13
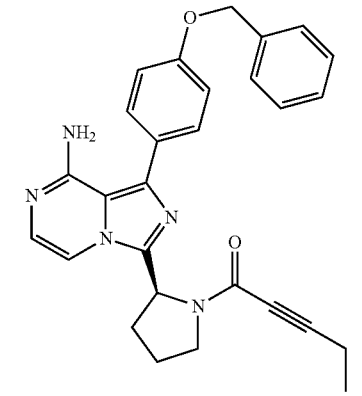
Compound 14
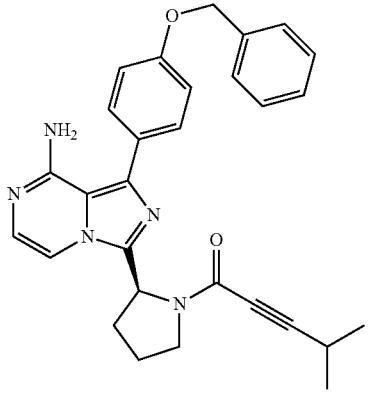

Compound 15
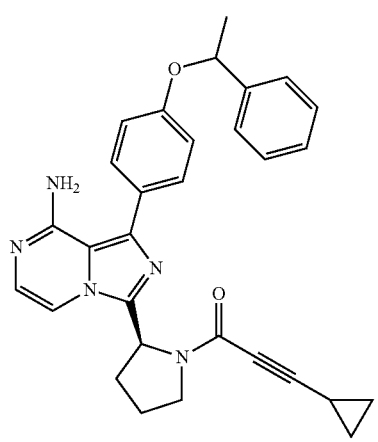
Compound 16
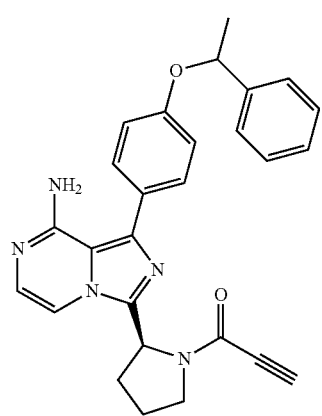
Compound 18
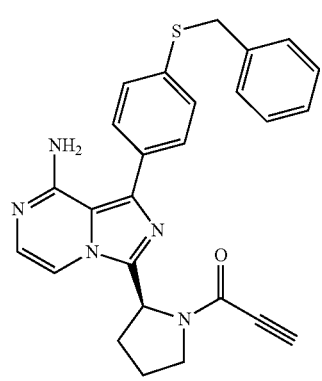
Compound 19
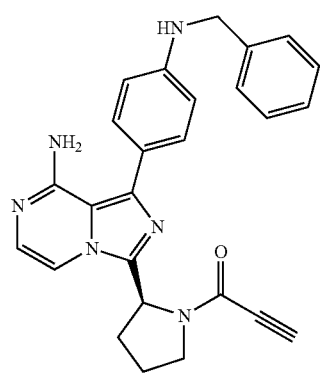
Compound 20
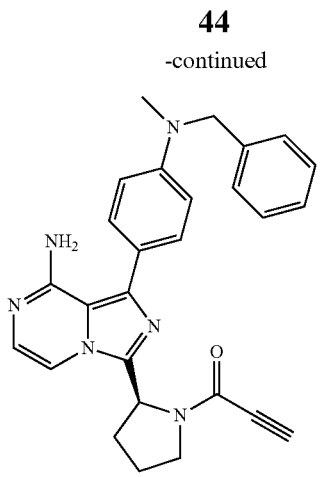
Compound 22
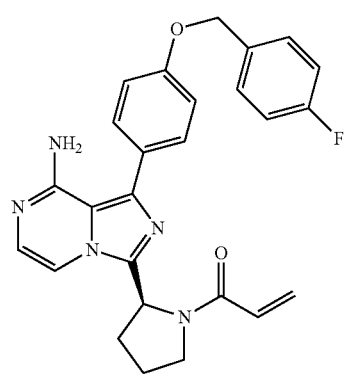
Compound 23
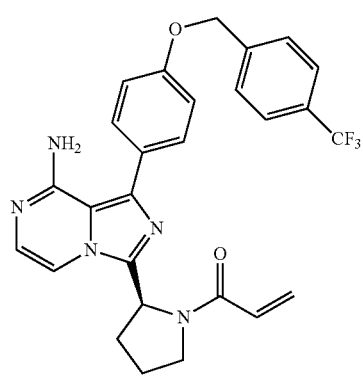
Compound 24
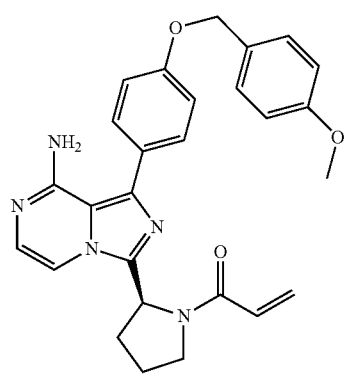

Compound 26
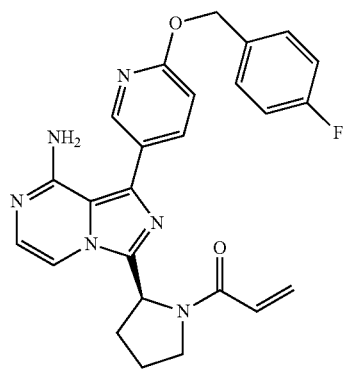
Compound 27
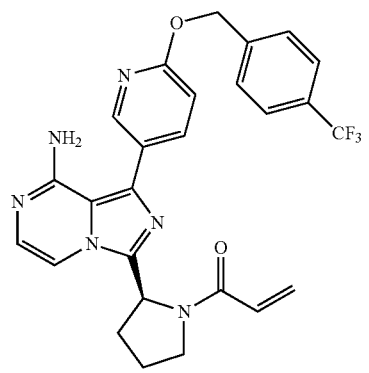
Compound 28
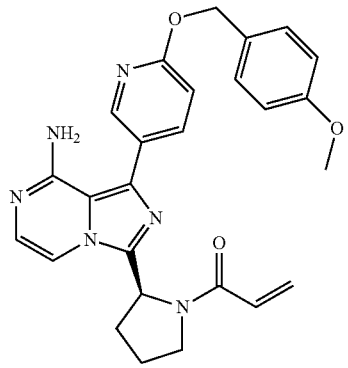
Compound 30
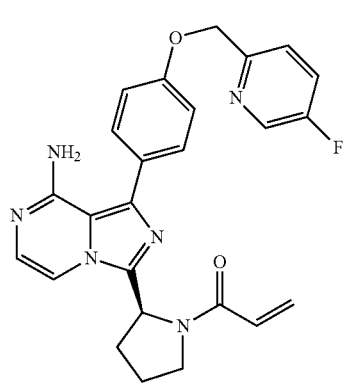
Compound 31
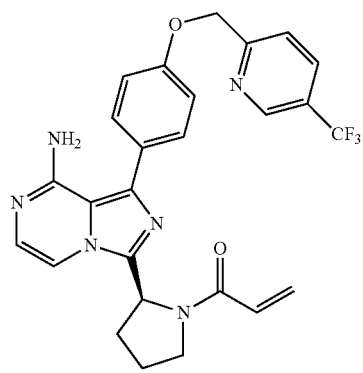
Compound 32
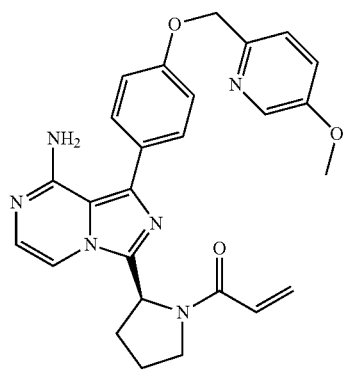
Compound 33
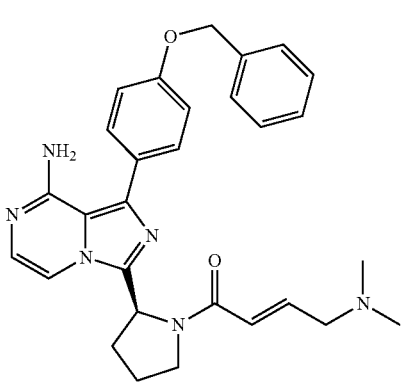
Compound 34
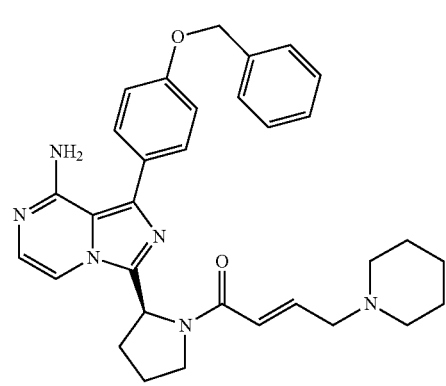

Compound 35

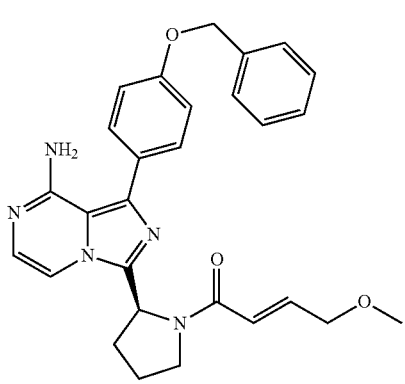

Compound 36

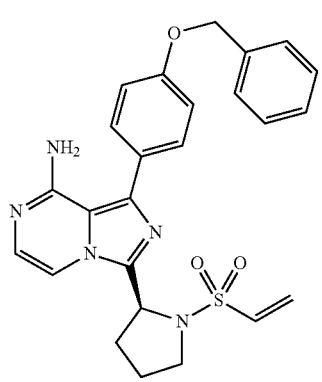

Example 11: Bioactivity Test

I. BTK Kinase Activity inhibition Assay

1. Assay Method

Activity of BTK protein kinase was tested by Caliper mobility shift assay (referring to J Biomol Screen 14:31, 2009). The compound of the present disclosure was dissolved in DMSO and then diluted 10-fold with kinase buffer solution (50 mM HEPES-pH 7.5, 0.0015% Brij-35, 10 mM MgCl$_2$, 2 mM DTT). 5 μl of 10% DMSO with 5-fold final reaction concentration of the compound dissolved was added into a 384-well plate, and a control well without the compound and a control well without kinase activity were respectively added 5 μl of 10% DMSO. 10 μl of BTK kinase solution (BTK, Cat. No. 08-080, Carna) with 2.5-fold final reaction concentration was added and mixed with the compound and then incubated for 10 minutes at room temperature, wherein the control well without kinase activity was added 10 μl of kinase buffer solution. 10 μl of a substrate solution of a substrate FAM-labeled SRCtide peptide (Biochem, Cat. No. 112394) and ATP (90 μM) with 2.5-fold final reaction concentration was further added to start the reaction. Then incubation was performed for 10 minutes at room temperature. After incubation for 1 hour 28° C., 25 μl of stopping solution (100 mM HEPES, pH 7.5, 0.015% Brij-35, 0.2% Coating Reagent #3, 50 mM EDTA) was added to terminate the reaction. The conversion ratio data was read on Caliper EZ Reader II (Caliper Life Sciences). The inhibition ratio was calculated and the calculation formula is: inhibition ratio %=(max-conversion)/(max-min)×100 %.

2. Assay Results

The compound of the present disclosure can strongly inhibit the BTK activity. The activities of the representative compounds of the present disclosure presented in BTK tests are listed in Table 1. In these tests, the following levels are used: with respect to IC$_{50}$, I>750 nM, 750 nM≥II>300 nM, 300 nM≥III>100 nM, IV≤100 nM.

TABLE 1

| Kinase activity inhibition results | | | |
|---|---|---|---|
| compound | BTK | compound | BTK |
| 1 | IV | 2 | I |
| 3 | I | 5 | II |
| 6 | I | 9 | I |
| 17 | II | 21 | IV |
| 25 | IV | 29 | III |
| ACP-196 | IV | | |

II. Inhibition Assay of Nonspecific Kinase EGFR, Tec, Txk, and ITK

1. Assay Method (1) EGFR Activity Inhibition Assay

In the case of Km ATP, EGFR T790M/L858R protein kinase activity was tested by Caliper mobility shift assay (referring to J Biomol Screen 14:31, 2009).

Assay method: the compound to be tested was dissolved in DMSO and then diluted with a kinase buffer solution (50 mM HEPES-pH7.5, 0.0015% Brij-35, 10 mM MgCl$_2$, 2 mM DTT). 5 μl of 10% DMSO with 5-fold final reaction concentration of the compound dissolved was added into a 384-well plate, a control well without the compound was added 5 μl of 10% DMSO, and a control well without kinase activity was added 5 μl of the kinase buffer solution. After adding 10 μl of 2.5-fold diluted EGFR (Cama, Cat. No 08-115, Lot. 13-CBS-0005M) kinase solution, the incubation was performed for 10 minutes at room temperature, and 10 μl of 2.5-fold diluted substrate solution Peptide FAM-P22 (GL Biochem, Cat. No. 112393, Lot. No. P130408-ZB112393) was further added. After being incubated for 60 minutes at 28° C., 25 μl of stopping solution (100 mM HEPES, pH 7.5, 0.015% Brij-35, 0.2% Coating Reagent #3, 50 m MEDTA) was added to terminate the reaction. The conversion ratio data was read on Caliper EZ Reader II (Caliper Life Sciences). The conversion ratio was converted to the inhibition ratio data.

A curve was plotted with the concentration of the compound and the inhibition ratio as the abscissa and ordinate values. XLFit excel add-in version 4.3.1 software was used to fit the curve and calculate IC$_{50}$. Inhibition ratio %=(max-conversion ratio)/(max-min)×100, wherein max refers to the conversion ratio of the control well in which the compound is absent in DMSO and min refers to the conversion ratio of the control well without kinase activity.

(2) Tec, Txk, and ITK Activities Inhibition Assay

The inhibitory activities of the compound to Tec, Txk, and ITK of human were performed by Eurofins Pharma Discovery Services UK Limited (UK) of the United Kingdom. In the case of Km ATP, the radioactive protein kinase method was adopted by the test. The kinase was diluted with buffer solution (20 mM MOPS, 1 mM EDTA, 0.01% Brij-35, 5% Glycerol, 0.1% 6-mercaptoethanol, 1 mg/mL BSA) before the reaction. The compound was dissolved in 100% DMSO and was of 50-fold final reaction concentration.

ITK reaction solution included 8 mM MOPS pH 7.0, 0.2 mM EDTA, 0.33 mg/mL myelin basic protein, 10 mM magnesium acetate, and [γ-$^{33}$P]-ATP (about 500 cpm/pmol), 200 μM ATP-Mg was added, after mixing, the reaction was started, the incubation was performed for 40 minutes at room temperature, and 3% phosphoric acid solution was added to terminate the reaction. 10 µl (reaction solution) was placed on P30 filtration membrane, washed with 75 mM phosphoric acid for 5 minutes, and dried with methanol for one time, and then scintillation counting was performed.

Active type Tex reaction solution contained 8 mM MOPS pH 7.0, 0.2 mM EDTA, 1 mM $Na_3VO_4$, 5 mM Na-6-phosphoglycerol, 400 µM EFPIYDFLPAKKK, 10 mM magnesium acetate, and [γ-$^{33}$P]-ATP (about 500 cpm/pmol), 120 µM ATP-Mg was added, after mixing, the reaction was started, the incubation was performed for 40 minutes at room temperature, and 3% phosphoric acid solution was added to terminate the reaction. 10 µl (reaction solution) was placed on P30 filtration membrane, washed with 75 mM phosphoric acid for 5 minutes, and dried with methanol for one time, and then scintillation counting was performed.

TxK reaction solution contained 8 mM MOPS pH 7.0, 0.2 mM EDTA, 250 µM GEEPLYWSFPAKKK, 10 mM magnesium acetate, and [γ-$^{33}$P]-ATP (about 500 cpm/pmol), 200 µM ATP-Mg was added, after mixing, the reaction was started, the incubation was performed for 40 minutes at room temperature, and 3% phosphoric acid solution was added to terminate the reaction, 10 µl (reaction solution) was placed on P30 filtration membrane, washed with 75 mM phosphoric acid for 5 minutes, and dried with methanol for one time, and then scintillation counting was performed.

2. Assay Results

The inhibitory activities of compounds to EGFR are shown in Table 2. The first generation BTK inhibitor Ibrutinib is an EGFR inhibitor with a very high activity, Ibrutinib inhibit the wild type EGFR non-selectively, relating to that this drug causes human body alimentary canal side effect, skin papule, and the like. The second generation EGFR inhibitor ACP-196 has no effect to phosphorylation of EGER at Y1068 locus and Y1173 locus, so there is no significant inhibitory effect to EGFR when in high concentration. As the same as ACP-196, the compound 1 does not inhibit EGER and the possibility to cause the toxic and side effect related to the inhibition to EGER is very low.

TABLE 2 inhibitory activities of the compounds to EGFR

| compound | kinase | $IC_{50}$ (nM) |
|---|---|---|
| ACP-196 | EGFR | >10,000 |
| Ibrutinib | EGFR | 4.6 nM |
| Compound 1 | EGFR | >10,000 |

The inhibitory activities of compound 1 and ACP-196 to Itk, Tec, and Txk are shown in Table 3. The first generation BTK inhibitor Ibrutinib is non-specific to inhibition of BTK, except to have inhibitory effect to EGFR, the first generation BTK inhibitor can further strongly inhibit activities of kinases such as ITK, Tec, and Txk (Byrd J. C. et al. N Engl J Med 374: 323, 2016). The second generation BTK inhibitor ACP-196 has no significant inhibitory effect to ITK, Tec, and Txk, can block BTK, pathway non-selectively, but cannot destroy the pathway of key molecule maintaining blood platelets and immunologic function, thereby avoiding or reducing some untoward effects related to the treatment of cancer. As similar as ACP-196, the inhibitory activities of the compound 1 to ITK, Tec, and Txk are very low

TABLE 3 inhibitory activities of the compound 1 and ACP-196 to ITK, Tec, and Txk

| | $IC_{50}$ (nM) | |
|---|---|---|
| kinase | Compound 1 | ACP-196 |
| Itk (h) | >10,000 | >5,000 |
| Tec (h) activated | 218 | 194.7 |
| Txk (h) | 4541 | 5000 |

III. Tumor Cell Proliferation Inhibition Assay

1. Assay Method

Cell viability was evaluated by measuring a content of triphosadenine (ATP) by using CellTiter-Glo luminescent cell viability assay kit method (Promega, # G7572, Madison, Wis.). Diffuse large B cell lymphoma cell strain TMD-8 and HCC827 NSCL cell strains are purchased from Shanghai Fudan IBS Cell Center and American Type Culture Collection (ATCC). After the cells were digested from a cell culture dish by pancreatin and re-suspended by DPBS culture medium, a Scepter automatic cell counter (Millipore, # PHCC00000) was used for counting to measure a cell density. The cells were diluted to be a solution containing 44,000 cells per milliliter. The cell solution with the adjusted density was added into a cell assay plate with 90 µl per well. The well plate was placed to an incubator with 5% $CO_2$ at 37° C. to be incubated for 24 hours and then added with the compound to be tested with different concentrations. The cells and the compound were together incubated for 72 hours in the presence of 10% fetal calf serum. The content of ATP was measured by using CellTiter-Glo® Luminescent Cell Viability Assay kit (referring to manufacturer's instruction) to evaluate the inhibition to the cell growth. Briefly speaking, each well was added with 30 µl of CellTiter-Glo® reagent, the plate was shaken for 10 minutes to induce the cells to be lysed, and fluorescence signal was detected and recorded by fluorescencelchemiluminescence analyzer Fluoroskan Ascent FL (Thermo Scientific Fluoroskan Ascent FL). The maximal signal value was obtained from cells processed by dimethyl sulfoxide (DMSO) for 72 or 120 hours. The minimal signal value obtained from separate culture medium (wherein the number of cells was zero) was defined as 0. Inhibition ratio %=(maximal signal value−compound signal value)/(maximal signal value−minimal signal value)×100%. The data was processed by using GraphPad Prism V5.0 (GraphPad Software San Diego, Calif.) software. $IC_{50}$ value was fitted and calculated via S-shaped dose-response curve.

2. Assay Results

The anti-proliferative activities of the compounds of the present disclosure in the cell-based test are listed in Table 4. In these tests, the following levels are used: with respect to $IC_{50}$, I>10 µM, 10 µM≥II>1 µM, 1 µM, 1 µM≥III>0.5 µM, 0.5 µM≥IV>0.1 µM, and V≤0.1 µM. The compounds of the present disclosure have very strong anti-proliferative activities to tumor cell such as TMD-8 while has weaker or no activities to HCC827 NSCLC cell. HCC827 cell strain carries EGFR exon 19 del and is sensitive to EGFR inhibitor. The assay results show that the compounds of the present disclosure have good selectivity.

TABLE 4 tumor cell proliferation inhibition results

| Compound | TMD-8 | HCC827 |
|---|---|---|
| 1 | V | I |
| 2 | IV | II |
| 3 | IV | I |
| 6 | IV | I |
| 21 | V | I |
| 25 | V | I |
| 29 | V | II |
| ACP-196 | V | I |

IV. Pharmacokinetic (PK) Assay

1. Assay Method

A male SD rat with 250-300 g of weight was fasted overnight before the assay. The compound to be tested was dissolved in 30% sulfobutyl ether-β-cyclodextrin (SBE-β-CD) and intragastrically administrated to the rat by 20 mg/kg of dosages. Take blood at $15^{th}$ minute, $30^{th}$ minute, and $1^{st}$, $2^{nd}$, $3^{rd}$, $4^{th}$, $6^{th}$, $8^{th}$, and $24^{th}$ hours after the administratation, and about 0.3 mL of blood was taken at each time point. The blood samples were placed into centrifuge tubes containing K2-EDTA (dipotassium ethylene diamine tetraacetate) and plasma was taken via centrifugal treatment (2,000 g, 10 minutes, 4° C.) and stored in a −80° C. of ultra low temperature refrigerator. 50 μL of plasma sample was mixed with 50 μL of internal standard (IS) and extracted with ethyl acetate. After vacuum dried, the residue was re-dissolved in acetonitrile The sample was filtered and injected into LC-MS/MS to be analyzed.

2. Assay Results

FIG. 1 shows plasma concentration-time curves of rats respectively orally administered with the compound 1 and ACP-196 (20 mg/kg). Table 5 shows pharmacokinetic parameters of the compound 1 and ACP-196 in the bodies of the rats.

As shown in FIG. 1 and Table 5, the half-life of the compound 1 in the body of the rat is 4.2 hours, the half-life of the ACP-196 is 7.9 hours, while $C_{max}$ and AUC of the compound 1 are more than double that of ACP-196. The compound 1 has been well adsorbed in the body of the rat and has a high plasma exposure amount. ACP-196, as a irreversible BTK inhibitor, is more safe and effective than the first generation BTK inhibitor Ibrutinib, which is believed to be related with the short half-life and high plasma exposure amount of ACP-196 except for the high selectivity of ACP-196 to BTK (Byrd J. C. et al. N Engl J Med 374: 323, 2016). The compound 1 has shorter half-life and higher plasma exposure amount as compared to ACP-196 and hence is possibly more safe and effective.

TABLE 5 pharmacokinetic parameters of the compound 1
and ACP-196 in the bodies of the rats
(20 mg/kg oral adminsteration)

| PK parameters | units | Compound 1 | ACP-196 |
|---|---|---|---|
| $t_{1/2}$ | h | 4.2 | 7.9 |
| $T_{max}$ | h | 0.5 | 0.5 |

TABLE 5-continued pharmacokinetic parameters of the compound 1
and ACP-196 in the bodies of the rats
(20 mg/kg oral adminsteration)

| PK parameters | units | Compound 1 | ACP-196 |
|---|---|---|---|
| $C_{max}$ | ng/mL | 1540 | 667.7 |
| $AUC_{0-24}$ | ng/mL × h | 3478 | 1299.7 |
| $AUC_{inf}$ | ng/mL × h | 3490 | 1403.5 |

Note:
in the table, $T_{max}$ refers to a time to peak, $C_{max}$ refers to a maximal plasma concentration, $T_{1/2}$ is a half-life, $AUC_{0-24}$ refers to an area under the 0-24 hours time-concentration curve, and $AUC_{inf}$ refers to an area under the 0-Inf time-concentration curve.

V. Tumor Model Pharmacodynamic Assay

1. Assay Method

The dose-effect relationship of inhibition of the compound to tumor growth in a diffuse large B cell lymphoma cell strain TMD-8 transplanted tumor model was studied in the present assay. When volume of TMD-8 tumor reached around 200 $mm^3$, the animals were divided into four oral administration groups, i.e. vehicle control group and 50 mg/kg, 100 mg/kg, and 200 mg/kg of compound 1 oral administration groups (n=8/roup). The compound 1 was dissolved in 30% sulfobutyl ether-β-cyclodextrin (SBE-β-CD) and 1.0 mol equivalent hydrochloric acid (pH 3-4) and intragastrically administered by 10 mL/kg once a day continually for 21 days.

The tumor volume was measured, and the relative tumor volume (RTV) and the relative tumor volume increased ratio were calculated. $RTV=V_t/V_0$, wherein $V_t$ is the average value of the tumor volume at $t^{th}$ day after the grouping and administrating, and $V_0$ is the average value of the tumor volume at the grouping day. T/C=treatment group RTV/control group RTV×100%.

2. Assay Results

Figure 2:
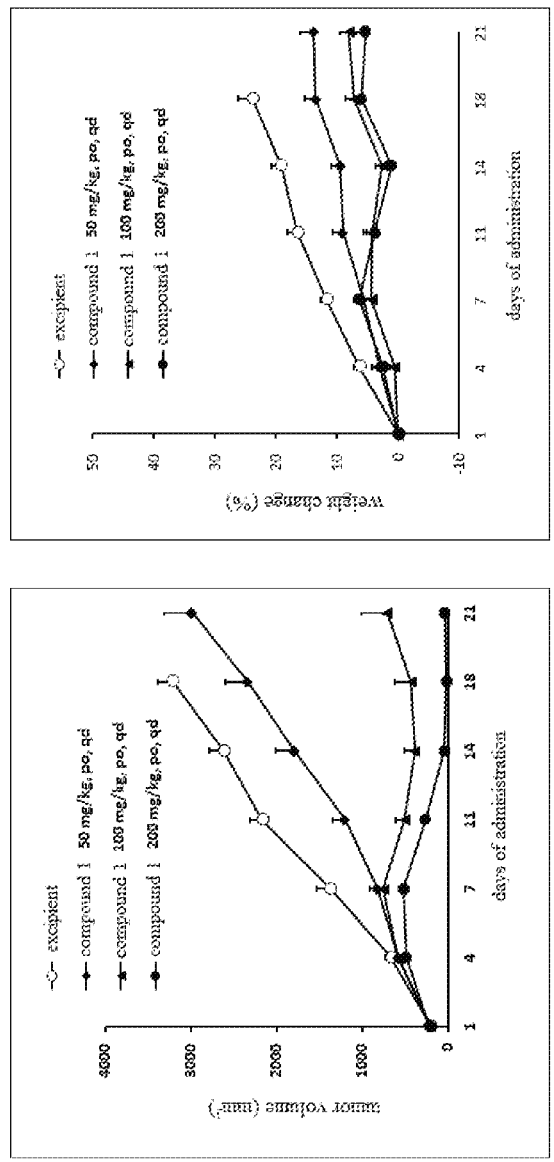

After administered to the vehicle group for 18 days, the assay was stopped since the tumor volume exceeded 3000 $mm^3$. FIG. 2 shows dose-response relationship of inhibition of the compound 1 to the growth of TMD-8 lymphoma cell strain transplanted tumor, wherein FIG. 2A shows the change of the tumor volume of each group of mice, and FIG. 2B shows the change of weight of the each group of mice. As shown in the figures, after administered the compound 1 for 18 days, 50 mg/kg dosage administration can mildly inhibit the tumor growth (T/C is 71%, p<0.05); 100 mg/kg dosage administration can arrest the tumor growth (T/C is 7%, p<0.001), and 200 mg/kg dosage administration can cause the tumor to be substantially disappeared (T/C is −91%, P<0.001). The weight of the animal of each administration group was increased as compared to that before the administration. The weights were increased more obviously in the vehicle group and the low dosage group, which may be relevant to the rapid growth of the tumor. The result shows that the compound 1 can dosage-dependently inhibit the growth of TMD-8 transplanted tumor by oral administration.

Although specific embodiments of the present invention have been described in detail, it will be understood by those skilled in the art that according to all of the teachings publicly known in the art, various modifications and substitutions of those details may be made, which will be within the scope of the present invention. The scopes of the present invention are defined by the accompanying claims and any equivalents thereof.

What is claimed is:

1. A compound having a structure as represented by formula (I), a pharmaceutically acceptable salt thereof, a stereoisomer thereof:

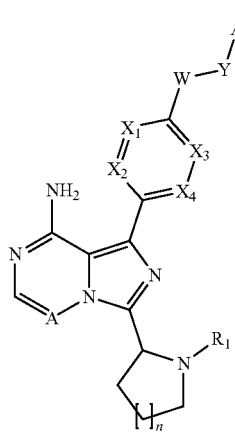
(I)

wherein,
A is selected from CH or N;
n is 0, 1, 2, or 3;
$R_1$ is selected from the following groups:

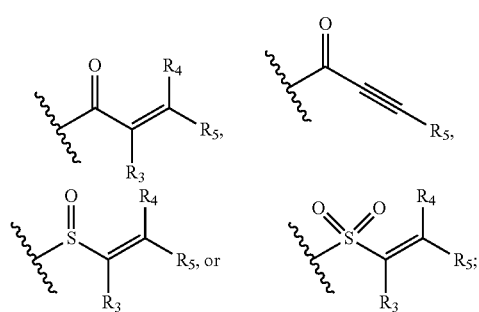

wherein $R_3$ and $R_4$ are each independently selected from H and $C_1$-$C_6$ alkyl;
$R_5$ is selected from the group consisting of H, $C_1$-$C_6$ alkyl, $C_3$-$C_6$ cycloalkyl, $C_1$-$C_4$ alkyl substituted with $C_1$-$C_3$ alkoxy, $C_1$-$C_4$ alkyl substituted with amino, $C_1$-$C_4$ alkyl substituted with $C_1$-$C_3$ alkyl amino, $C_1$-$C_4$ alkyl substituted with di($C_1$-$C_3$ alkyl) amino, and $C_1$-$C_4$ alkyl substituted with heterocyclic group;
$X_1$, $X_2$, $X_3$ and $X_4$ are each independently selected from the group consisting of $C(R_2)$ and N;
$R_2$ is selected from the group consisting of H, halogen atom, $C_1$-$C_6$ alkyl, $C_1$-$C_6$ alkoxy, and halogenated $C_1$-$C_6$ alkyl;
W and Y are each independently selected from the group consisting of O, N($R_6$), S and $C_1$-$C_6$ alkylene, and at least one of W and Y is selected from $C_1$-$C_6$ alkylene;
$R_6$ is selected from H or $C_1$-$C_6$ alkyl; and
Ar is selected from phenyl or 5 to 6 membered heteroaryl, optionally, the phenyl or 5 to 6 membered heteroaryl is substituted with a group selected from the group consisting of halogen atom, $C_1$-$C_6$ alkyl, $C_1$-$C_6$ alkoxy, and halogenated $C_1$-$C_6$ alkyl.

2. The compound of claim 1, the pharmaceutically acceptable salt thereof, or the stereoisomer thereof, wherein $X_1$, $X_2$, $X_3$ and $X_4$ are each selected from $C(R_2)$; or, one of $X_1$, $X_2$, $X_3$ and $X_4$ is N and the remaining are each selected from $C(R_2)$.

3. The compound of claim 1, the pharmaceutically acceptable salt thereof, or the stereoisomer thereof, wherein the compound has a structure as represented by formula (II):

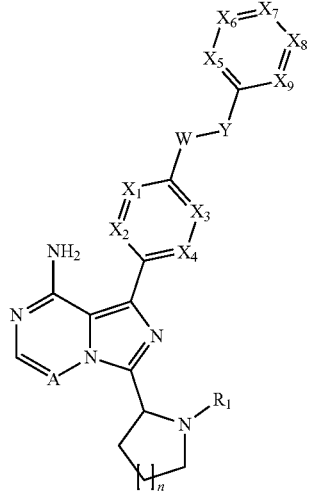
(II)

wherein $X_5$, $X_6$, $X_7$, $X_8$ and $X_9$ are each independently selected from $C(R_7)$ or N;
$R_7$ is selected from the group consisting of H, halogen atom, $C_1$-$C_6$ alkyl, $C_1$-$C_6$ alkoxy, and halogenated $C_1$-$C_6$ alkyl.

4. The compound of claim 1, the pharmaceutically acceptable salt thereof, or the stereoisomer thereof, wherein W is selected from O, N($R_6$) or S, $R_6$ is selected from H or $C_1$-$C_6$ alkyl; Y is selected from $C_1$-$C_6$ alkylene.

5. The compound of claim 1, the pharmaceutically acceptable salt thereof, or the stereoisomer thereof, wherein n is 1 or 2;

a chiral carbon atom in

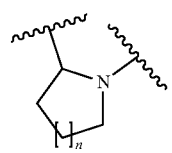

is of a sinister configuration.

6. The compound of claim 1, the pharmaceutically acceptable salt thereof, or the stereoisomer thereof, wherein $R_1$ is selected from the following groups:

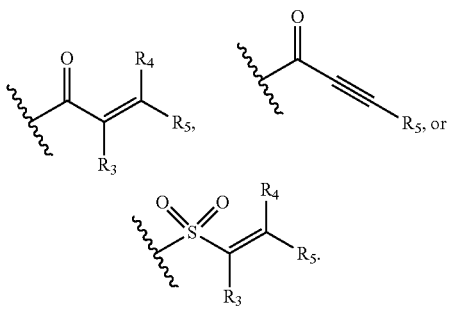

7. The compound of claim 1, the pharmaceutically acceptable salt thereof, or the stereoisomer thereof, wherein $R_1$ is

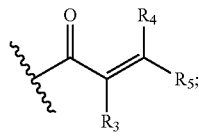

$R_3$ is H;
$R_4$ is H;
preferably, $R_5$ is selected from the group consisting of H, $C_1$-$C_4$ alkyl substituted with $C_1$-$C_3$ alkoxy, $C_1$-$C_4$ alkyl substituted with di($C_1$-$C_3$ alkyl) amino, and $C_1$-$C_4$ alkyl substituted with 5 to 6 membered saturated nitrogen-contaning heterocyclic group.

8. The compound of claim 1, the pharmaceutically acceptable salt thereof, or the stereoisomer thereof, wherein $R_1$ is

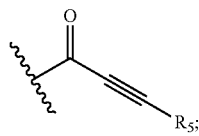

$R_5$ is selected from the group consisting of H, $C_1$-$C_4$ alkyl and $C_3$-$C_6$ cycloalkyl.

9. The compound of claim 1, the pharmaceutically acceptable salt thereof, or the stereoisomer thereof, wherein,
A is CH;
$X_1$, $X_2$, $X_3$ and $X_4$ are each CH; or
$X_1$ is N, while $X_2$, $X_3$ and $X_4$ are each CH; or
$X_2$ is N, while $X_1$, $X_3$ and $X_4$ are each CH; or
$X_3$ is N, while $X_1$, $X_2$ and $X_4$ are each CH; or
$X_4$ is N, while $X_1$, $X_2$ and $X_3$ are each CH;
W is O, N($R_6$) or S, wherein $R_6$ is selected from H or $C_1$-$C_3$ alkyl;
Y is selected from $C_1$-$C_3$ alkylene;
n is 1;
$R_1$ is selected from

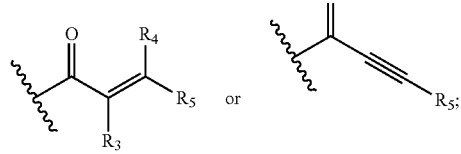

wherein $R_3$ is H;
$R_4$ is H;
$R_5$ is selected from the group consisting of H, $C_1$-$C_6$ alkyl, $C_3$-$C_6$ cycloalkyl, $C_1$-$C_4$ alkyl substituted with $C_1$-$C_3$ alkoxy, $C_1$-$C_4$ alkyl substituted with $C_1$-$C_3$ alkyl amino, $C_1$-$C_4$ alkyl substituted with di($C_1$-$C_3$ alkyl) amino, and $C_1$-$C_4$ alkyl substituted with 5 to 6 membered saturated nitrogen-contaning heterocyclic group;
Ar is selected from phenyl or 6 membered nitrogen-containing heteroaryl, optionally, the phenyl or 6 membered nitrogen-containing heteroaryl is substituted with a group selected from the group consisting of halogen atom, $C_1$-$C_6$ alkyl, $C_1$-$C_6$ alkoxy, and halogenated $C_1$-$C_6$ alkyl.

10. The compound of claim 1, the pharmaceutically acceptable salt thereof, or the stereoisomer thereof, wherein the compound has a structure as represented by formula (III):

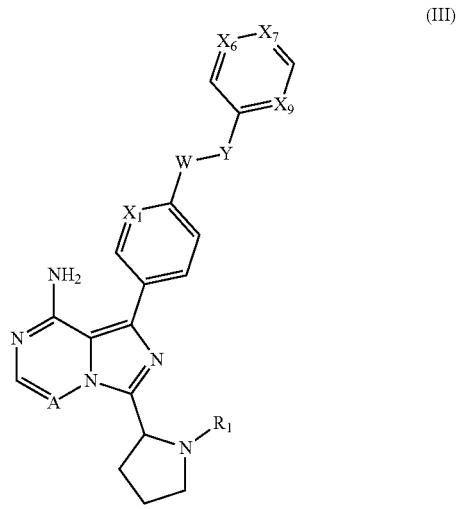

(III)

wherein $X_1$ is CH or N;
W is selected from O, S and N($R_6$), $R_6$ is selected from H or methyl;
Y is selected from the group consisting of methylene, 1,1-ethylidene and 1,2-ethylidene;
$X_6$ and $X_7$ are each independently selected from C($R_7$), wherein $R_7$ is selected from the group consisting of H, F, trifluoromethyl and methoxyl;
$X_9$ is selected from CH or N;
$R_1$ is

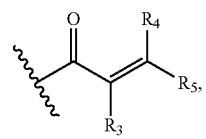

wherein $R_3$ is H, $R_4$ is H, and $R_5$ is selected from the group consisting of H, methyl substituted with methoxyl, methyl substituted with dimethyl amino, and methyl substituted with piperidyl; or $R_1$ is

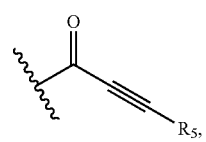

wherein $R_5$ is selected from the group consisting of H, methyl, ethyl, isopropyl and cyclopropyl; or $R_1$ is
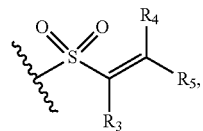
wherein $R_3$, $R_4$ and $R_5$ are each H.
11. The compound of claim 1, the pharmaceutically acceptable salt thereof, or the stereoisomer thereof, wherein the compound is selected from the group consisting of:
compound 1
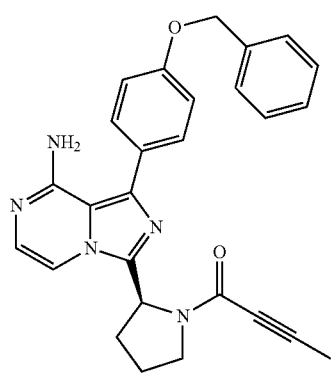
compound 2
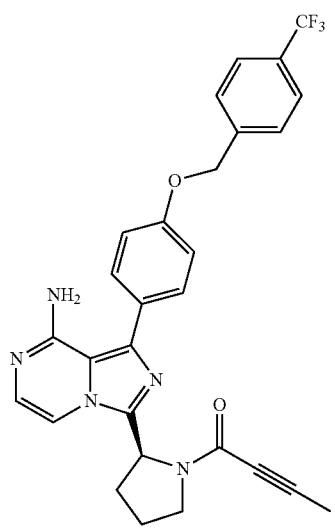
-continued
compound 3
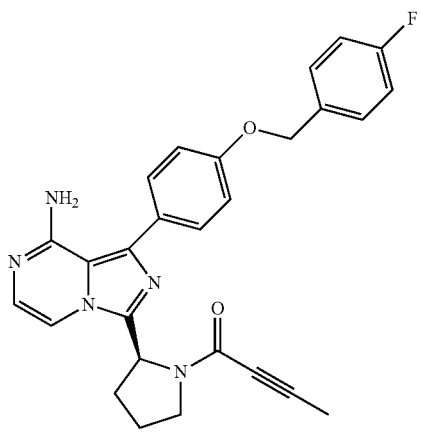
compound 4
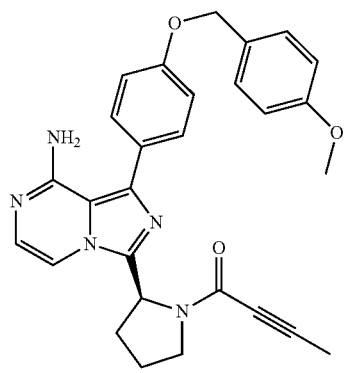
compound 5
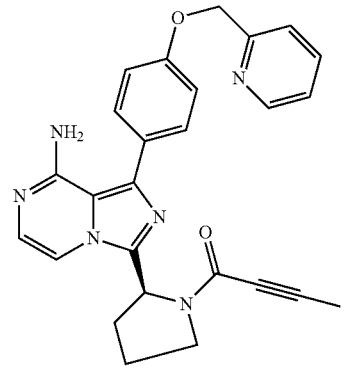
compound 6
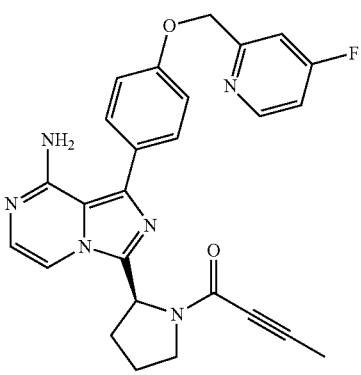

compound 7
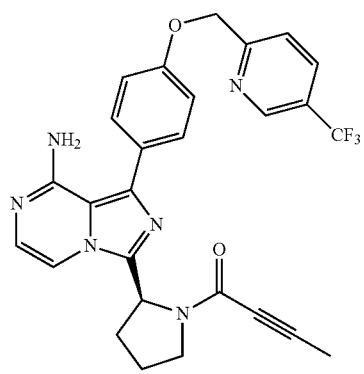
compound 8
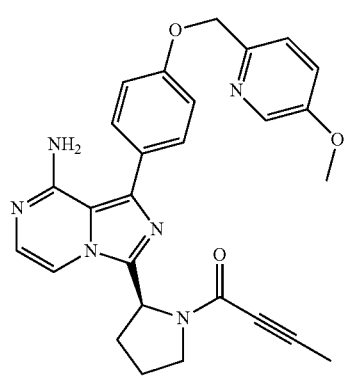
compound 9
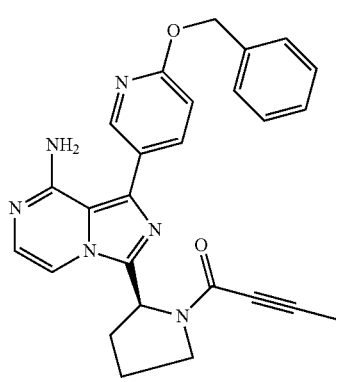
compound 10
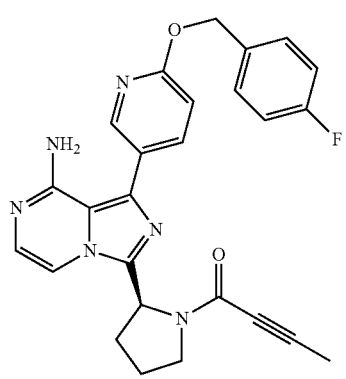
compound 11
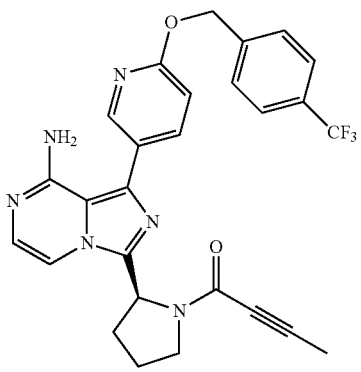
compound 12
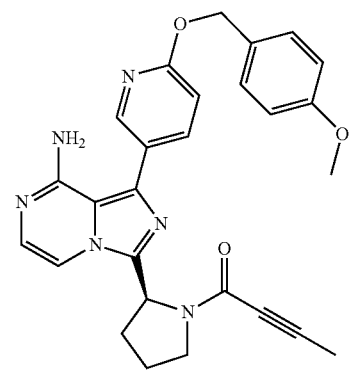
compound 13
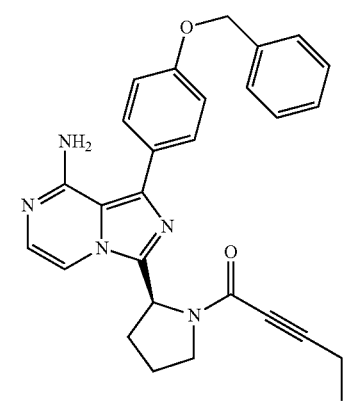
compound 14
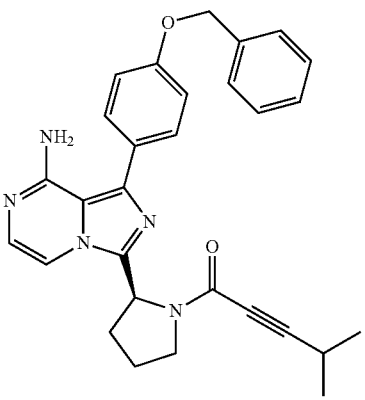

compound 15
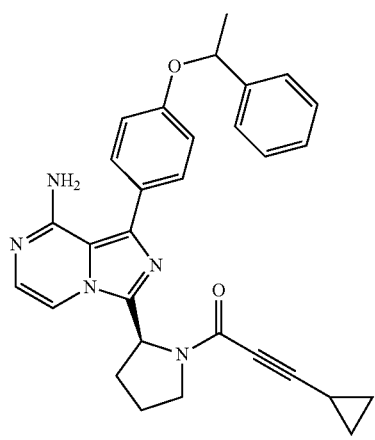
compound 16
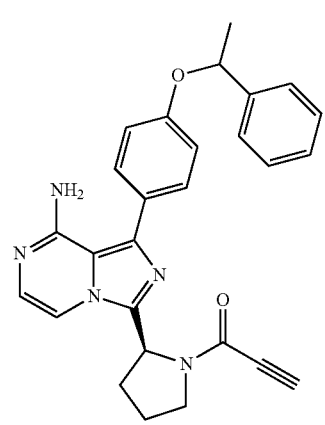
compound 17
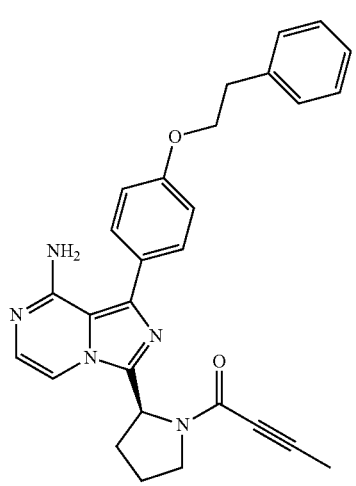
compound 18
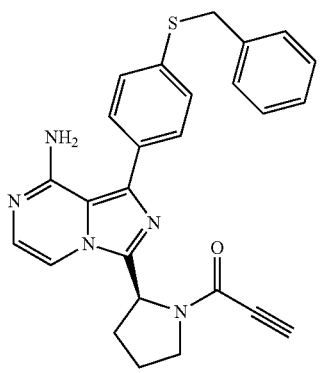
compound 19
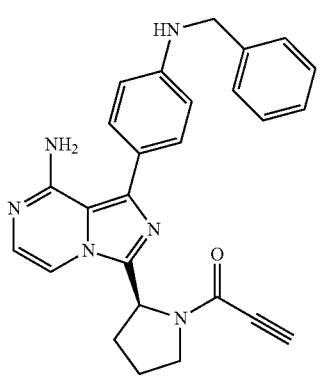
compound 20
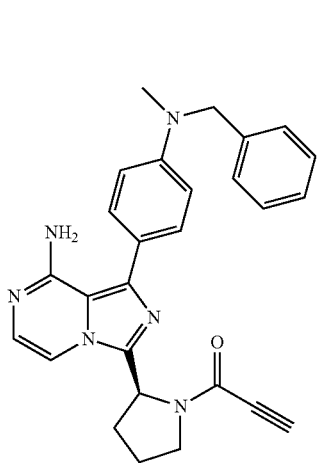
compound 21
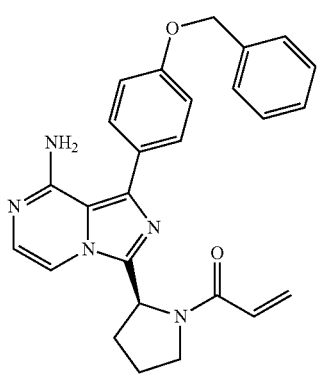

compound 22
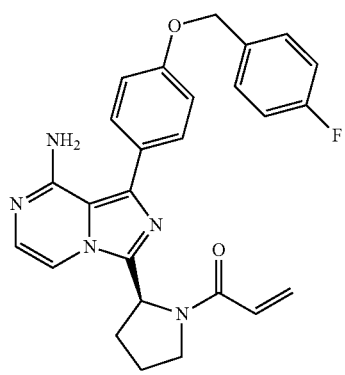
compound 23
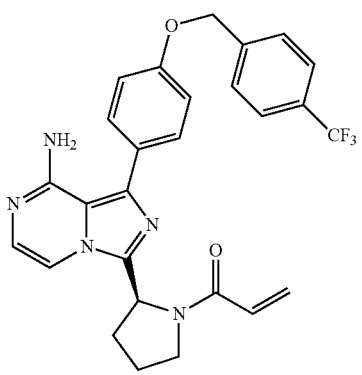
compound 24
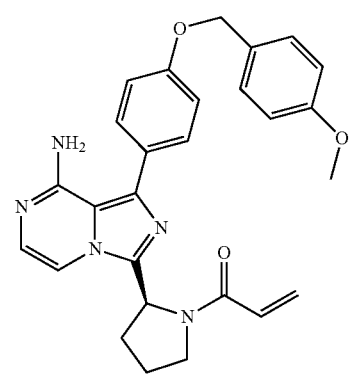
compound 25
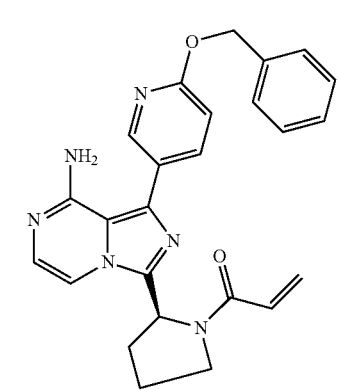
compound 26
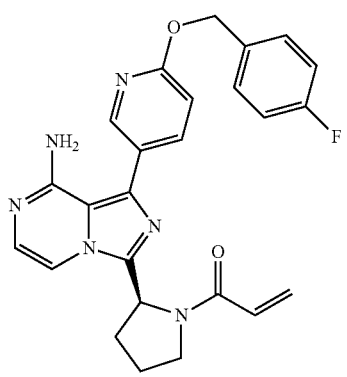
compound 27
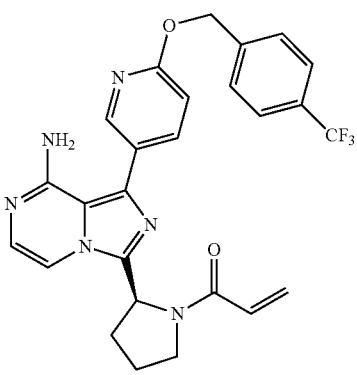
compound 28
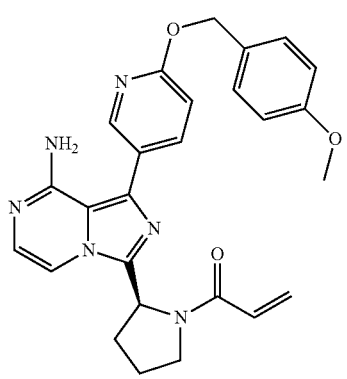
compound 29
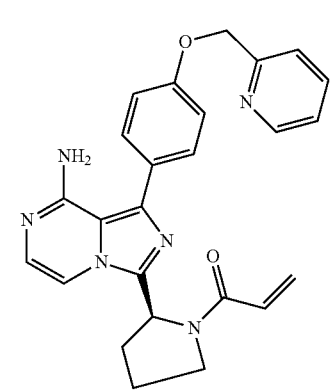

-continued compound 30
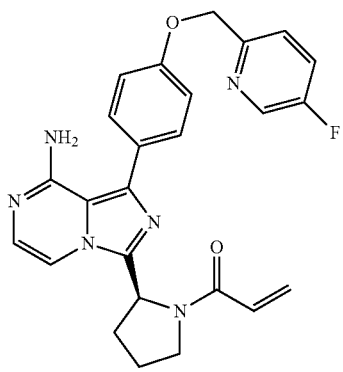

compound 31
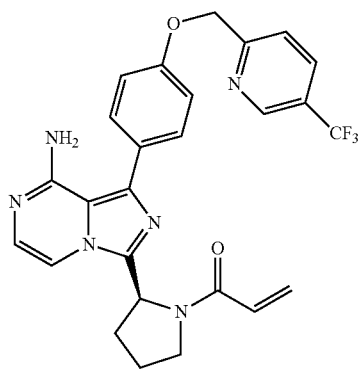

compound 32
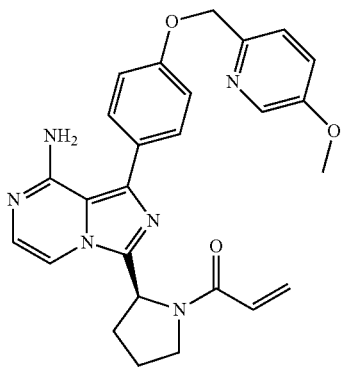

compound 33
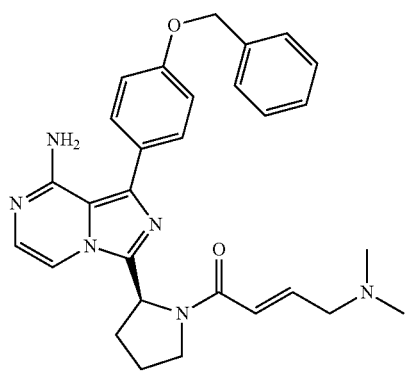

-continued compound 34
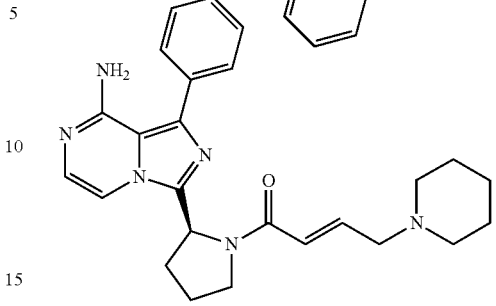

compound 35
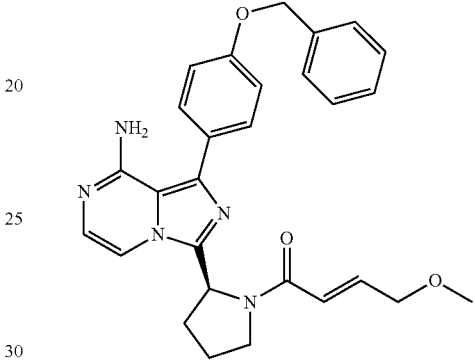

compound 36
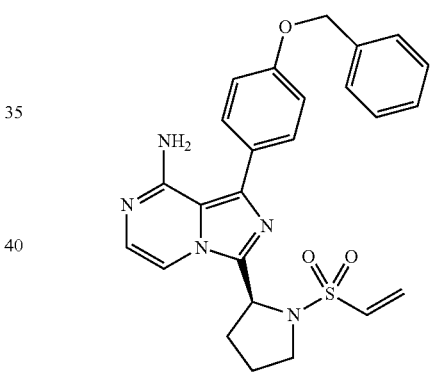

12. A pharmaceutical composition, comprising the compound of claim 1, the pharmaceutically acceptable salt thereof, or the stereoisomer thereof.

13. A method for treating a disease in a subject, the method comprising administering to the subject the pharmaceutical composition of claim 12, wherein the disease is tumor, inflammation, or autoimmune disease, and the tumor, the inflammation, or the autoimmune disease is treated by inhibition of BTK.

14. The compound of claim 2, the pharmaceutically acceptable salt thereof, or the stereoisomer thereof, wherein $X_1$, $X_2$, $X_3$ and $X_4$ are each CH; or, one of $X_1$, $X_2$, $X_3$ and $X_4$ is N and the remaining are each CH.

15. The compound of claim 3, the pharmaceutically acceptable salt thereof, or the stereoisomer thereof, wherein $X_5$, $X_6$, $X_7$, $X_8$ and $X_9$ are each selected from $C(R_7)$; or, one of $X_5$, $X_6$, $X_7$, $X_8$ and $X_9$ is N and the remaining are each selected from $C(R_7)$.

16. The compound of claim 3, the pharmaceutically acceptable salt thereof, or the stereoisomer thereof, wherein $X_5$, $X_6$, $X_7$, $X_8$ and $X_9$ are each CH; or one of $X_5$, $X_6$, $X_7$, $X_8$ and $X_9$ is $C(R_7)$, the remaining are each CH, and $R_7$ is selected from the group consisting of halogen atom, $C_1$-$C_6$ alkyl, $C_1$-$C_6$ alkoxy and halogenated $C_1$-$C_6$ alkyl.

17. The method of claim 13, wherein the disease is selected from the group consisting of B-cell Non-Hodgkin's lymphoma, primary macroglobulinemia, multiple myeloma, hairy cell leukemia, rheumatoid arthritis, lupus nephritis, and Sjogren's syndrome.

18. The method of claim 17, wherein the B-cell Non-Hodgkin's lymphoma is selected from the group consisting of refractory mantle cell lymphoma, chronic lymphocytic leukemia, and diffuse large B cell lymphoma.

19. The pharmaceutical composition of claim 12, wherein the pharmaceutical composition is a BTK inhibitor.

* * * * *